United States Patent
Shiratori et al.

[11] Patent Number: 5,974,160
[45] Date of Patent: Oct. 26, 1999

[54] MEASURING METHOD AND APPARATUS OF GLOSS IRREGULARITY AND PRINTING UNEVENNESS

[75] Inventors: Naoyuki Shiratori, Tokyo; Hidekazu Ishimura, Fuji; Nobuko Yoshidomi, Tokyo, all of Japan

[73] Assignee: Asahi Kasei Kogyo Kabushiki Kaisha, Osaka, Japan

[21] Appl. No.: 08/635,937
[22] PCT Filed: Oct. 26, 1994
[86] PCT No.: PCT/JP94/01795
 § 371 Date: Apr. 25, 1996
 § 102(e) Date: Apr. 25, 1996
[87] PCT Pub. No.: WO95/12120
 PCT Pub. Date: May 4, 1995

[30] Foreign Application Priority Data

Oct. 26, 1993 [JP] Japan .................................. 5-267477

[51] Int. Cl.⁶ .................................................. G06K 9/00
[52] U.S. Cl. ..................... 382/112; 382/108; 356/369; 356/371; 250/559.01; 250/559.04; 250/559.05; 250/559.07
[58] Field of Search ..................................... 382/108, 112; 356/369, 371, 445, 446, 448, 237; 250/559.18, 559.01, 559.04, 559.05, 559.07, 559.08, 559.09

[56] References Cited

U.S. PATENT DOCUMENTS

| | | | |
|---|---|---|---|
| 4,710,963 | 12/1987 | Chapman et al. | 356/71 |
| 4,736,315 | 4/1988 | Ozaki et al. | 356/355 |
| 4,931,657 | 6/1990 | Houston et al. | 356/369 |
| 4,966,455 | 10/1990 | Avni | 356/446 |
| 5,033,095 | 7/1991 | Marcantonio | 356/237 |
| 5,146,097 | 9/1992 | Fujiwara et al. | 356/446 |
| 5,182,775 | 1/1993 | Matsui et al. | 382/152 |
| 5,278,411 | 1/1994 | Popil et al. | 250/330 |

FOREIGN PATENT DOCUMENTS

| | | |
|---|---|---|
| 60-024406 | 2/1985 | Japan . |
| 61-217708 | 9/1986 | Japan . |
| 1-245364 | 9/1989 | Japan . |
| 2-271211 | 11/1990 | Japan . |

OTHER PUBLICATIONS

Fujiwara, et al., "Measurement of Gloss Profile," Coating Conference, 1990, pp. 209–218.

MacGregor, et al, "Gloss Uniformity in Coated Paper—Measurements of commercial papers," Coating Conference, 1991, pp. 495–504.

Arai, "Relationship Between Coating Structure and Print Mottle," pp. 57–68.

Koskinen, et al., "Comparison of Test Methods for LWC Offset Paper with the Aim of Predicting Mottling Tendency," Paperi Ja Puu—Paper and Timber, vol. 74, No. 1, 1992, pp. 45–55.

*Primary Examiner*—Jon Chang
*Assistant Examiner*—Jingge Wu
*Attorney, Agent, or Firm*—Finnegan, Henderson, Farabow, Garret & Dunner, L.L.P.

[57] ABSTRACT

An outer surface of an object 23 is irradiated with visible light from a light source 21, and the reflected light is acquired by a TV camera 24. A two-dimensional image with gradation is Fourier transformed by an image analyzer 20. The brightness and darkness of the image are bipolarized using an emphasis coefficient in a predetermined wavelength range in the process of Fourier transform. The bright regions and dark regions forming closed regions are calculated separately as regions representing gloss irregularity or printing unevenness, thereby outputting a statistical parameter of the areas as a measured result.

16 Claims, 22 Drawing Sheets

1mm
TWO-DIMENSIONAL IMAGE

EMPHASIZED IMAGE

MEASURING METHOD AND APPARATUS OF GLOSS IRREGULARITY AND PRINTING UNEVENNESS

TECHNICAL FIELD

The present invention relates to a measuring method and apparatus of the gloss irregularity and printing unevenness which are measured quantitatively as one of the items of qualities

BACKGROUND ART

Recently, besides the gloss intensity of surfaces of products, the unevenness of gloss and that of printed coated paper or films have been regarded important as the quality of the products The qualities are, for example, "surface feeling" of coated paper, "flowmarks" of the surface of formed plastics, and "clear reflective property" of automobile applications About the surface feeling of coated paper, it is considered that the more uniform the gloss value of the product appearance, the better the surface feeling. The evaluation has been conventionally made by inspectors who conducts visual observation mainly of the sub-millimeter gloss irregularity on the coated paper. Alternatively, the following test methods have been proposed, in which images of product appearance are picked up with an image pickup device like a TV camera, and the luminance level distribution (the reflected light power) of the product appearance is calculated on the basis of the acquired images.

One of the methods remodeled a chromato-scanner to scan the surface of coated paper with a light flux of 0.4 mm$\phi$ at angles of incidence and reflection of 75 degrees, and has disclosed that the standard deviation of reflected light power has a relation to the rank order of visual inspection (H. Fujiwara et al., 1990, TAPPI Coat. Conf. Proc., 209 (1990)).

Another method is to obtain the correlation between the average of visually observed rank order and the result of the analysis of a two-dimensional image formed by surface reflection from printed paper, which was acquired by a CCD camera. This method has disclosed that the rank order exhibits good correlation with the reflected light power, that is, with the variation coefficient of gradation. However, it has been reported that there were many cases which exhibited no correlation about the gloss irregularity of white paper (M. A. MacGregor et al., 1991, TAPPI Coat. Conf. Proc., 495 (1991)).

Next, the printing unevenness of printed coated-paper will be explained. The printing unevenness is considered to increase with the ink density variation in neighborhoods in an area to be printed uniformly. The degree of unevenness is considered to correspond to the magnitude of difference among them. Since the printing unevenness is likely to appear in halftone regions of uniform ink density, the visual evaluation is carried out by an inspector on the halftone areas of the printed matter. Several measuring methods and devices have also been proposed to detect the printing unevenness.

One of the methods is to calculate areal ratios of individual dots in the halftone areas, and derive the coefficients of variation (Takao Arai, Magazine of the Paper and Pulp Engineering Institute, 43 575 (1989)), Another method is to conduct the line scanning of the series of dotted regions in a halftone portion by an image analyzer to digitize the regularity of density profile, thereby obtaining parameters of the printing unevenness (T. Koskinen et al., Paperi JaPuu 74 45 (1992)).

The visual inspections of the gloss irregularity and printing unevenness, however, lack quantitative accuracy because they depend on personal subjectivity, and hence it requires many professional inspectors to carry out objective judge on the quality of printing.

On the other hand, the above mentioned optical test methods of gloss irregularity have the following drawbacks.

Although the quantification of optical measurement of the gloss irregularity is tried using reflected light power distribution, it has a problem that the results do not necessarily coincide with those of the visual inspection. In particular, there are large errors in the optical method in the case where white paper surface feeling (the surface feeling before printing) is tested by measuring the power distribution of reflected light. This is because the intense diffused reflected light weakens the gloss irregularity associated with the true reflected light.

Moreover, in the optical test of the printing unevenness, there are some cases which do not coincide with the results of the visual inspection because the optical method measures ink density only.

Taking account of these facts, an object of the present invention is to provide an optical measuring method and apparatus of the gloss irregularity which can quantitatively express the measured results of the gloss irregularity with accuracy in terms of magnitude and distribution of the gloss irregularity rather than the power distribution of light, and to offer a measuring method and apparatus of the printing unevenness which can improve the accuracy by measuring the areas and distribution of uneven portions of ink density rather than by measuring the ink density itself.

Other objects and features of the present invention will be apparent from the following description, some of which will become clear by the description, or be understood by implementing the present invention. The objects and advantages of the present invention are implemented by the means recited in the claims and the combinations thereof.

DISCLOSURE OF THE INVENTION

An object of the present invention is to provide a measuring method and apparatus which makes it possible to measure the gloss irregularity and the printing unevenness more accurately than the conventional methods which utilize the power distribution of light and the density distribution of ink.

The measuring method of the gloss irregularity and printing unevenness in accordance with the present invention acquires an image of an inspection object with an image pickup device, and includes the following steps carried out by an image analyzer: detecting, in the acquired image, bright or dark regions forming closed regions as portions representative of the gloss irregularity and printing unevenness of the inspection object; obtaining the areas of the individual closed regions detected; calculating the distribution of the areas; and producing the calculation results as the measured results of quantified gloss irregularity and printing unevenness. The inventors of the present application have discovered that bright and dark portions form the closed regions in the acquired image because the gloss irregularity and the printing unevenness on the appearance of a product have greater differences in brightness and thickness than their surrounding regions. Thus, calculating the distribution of areas of these closed regions makes it possible to express quantitatively the measured results of the gloss irregularity and the printing unevenness.

More specifically, a first aspect of the present invention is characterized in that it acquires an image of an inspection object with an image pickup device, and by using an image analyzer, it detects, in an acquired image, bright regions or dark regions forming closed regions, the closed regions being considered to represent printing unevenness of the inspection object; obtains areas of the closed regions; calculates a distribution of the areas; and adopts a result of calculating as a quantified value of measured results of the printing unevenness.

A second aspect of the present invention is characterized, in addition to the first aspect of the present invention, in that the distribution of the areas is a mean of the areas or a standard deviation of the areas.

A third aspect of the present invention is characterized in that it acquires an image of an inspection object with an image pickup device, and using an image analyzer, it detects, in an acquired image, bright regions or dark regions forming closed regions, the closed regions being considered to represent printing unevenness of the inspection object; and calculates a product of a mean area of the closed regions and a standard deviation of areas of the closed regions as a qualified value representative of the printing unevenness A fourth aspect of the present invention is characterized in that an image of a surface of paper is acquired with an image pickup device, and using an image analyzer, it detects, in an acquired image, bright regions or dark regions forming closed regions; obtains areas of the closed regions; calculates a distribution of the areas; and adopts a result of the calculation as a quantified value representing the printing unevenness.

A fifth aspect of the present invention is characterized, in addition to the fourth aspect of the present invention, in that a kind of the paper is one of gloss tone coated paper, mat tone coated paper and a paperboard.

A sixth aspect of the present invention is characterized, in addition to the first, third and fourth aspects of the present invention, in that it emphasizes brightness and darkness of the acquired image in detecting the bright regions or the dark regions forming the closed regions.

A seventh aspect of the present invention is characterized in that it comprises: image pickup means for acquiring an image of an inspection object; detecting means for detecting, in an acquired image, bright regions or dark regions forming closed regions, the closed regions being considered to represent printing unevenness of the inspection object; area obtaining means for obtaining areas of the closed regions; calculating means for calculating a distribution of areas, and for outputting a calculating result as a measured result of the printing unevenness.

An eighth aspect of the present invention is characterized, in addition to the seventh aspect of the present invention, in that it further comprises a polarization filter which transmits only a diffused reflected light from the inspection object to the acquiring means.

A ninth aspect of the present invention is characterized in that it acquires an image of an inspection object with an image pickup device, and using an image analyzer, it detects, in the acquired image, bright regions or dark regions forming closed regions, the closed regions being considered to represent gloss irregularity of the inspection object; and calculates a product of a mean area of the closed regions and a standard deviation of areas of the closed regions as a qualified value representative of the gloss irregularity.

A tenth aspect of the present invention is characterized in that it acquires an image of a surface of mat paper with an image pickup device, and using an image analyzer, it detects, in an acquired image, bright regions forming closed regions, the closed regions being considered to represent gloss irregularity of the surface of the mat paper; obtains areas of the closed regions; calculates a distribution of the areas; and adopts a result of the calculation as a quantified value representing the gloss irregularity.

An eleventh aspect of the present invention is characterized in that it acquires an image of a surface of a paperboard with an image pickup device, and using an image analyzer, it detects, in an acquired image, dark regions forming closed regions, the closed regions being considered to represent gloss irregularity of the surface of the paperboard; obtains areas of the closed regions; calculates a distribution of the areas; and adopts a result of the step of calculating as a quantified gloss irregularity.

A twelfth aspect of the present invention is characterized, in addition to the eleventh aspect of the present invention, in that the distribution of the areas is a mean area or a standard deviation of the areas.

A thirteenth aspect of the present invention is characterized in that in a measuring method of gloss irregularity acquiring an image of a surface of paper with an image pickup device, and carrying out information processing on an acquired image with an image analyzer, thereby adopting a result of the information processing as a measuring result of the gloss irregularity, it provides the image analyzer with information on a kind of the paper for determining which one of bright regions and dark regions of the acquired image is to be employed, and the image analyzer detects, in the acquired image, closed regions of one of the bright regions or dark regions in accordance with the kind of the paper; obtains areas of the closed regions; calculates a distribution of the areas; and adopts a result of the step of calculating as a quantified gloss irregularity.

A fourteenth aspect of the present invention is characterized, in addition to the thirteenth aspect of the present invention, in that a kind of the paper is one of gloss tone coated paper, mat tone coated paper, and a paperboard.

A fifteenth aspect of the present invention is characterized, in addition to the fourteenth aspect of the present invention, in that the closed regions are dark regions of the acquired image in the gloss tone coated paper.

A sixteenth aspect of the present invention is characterized, in addition to the fourteenth aspect of the present invention, in that the closed regions are bright regions of the acquired image in the mat tone coated paper.

A seventeenth aspect of the present invention is characterized, in addition to the fourteenth aspect of the present invention, in that the closed regions are dark regions of the acquired image in the paperboard. An eighteenth aspect of the present invention is characterized, in addition to the ninth, tenth, eleventh and thirteenth aspects of the present invention, in that it emphasizes brightness and darkness of the acquired image in detecting the bright regions or dark regions which form the closed regions.

In the first, second and third aspects of the present invention, the accuracy of measurement is increased by grasping the printing unevenness in the form of the closed regions in the acquired image, and by expressing the degree of distribution of the areas of the closed regions in terms of, for example, the mean area, the standard deviation, the coefficient of variation, the number of white portions or dark portions per unit area, or the product of the mean area and the standard deviation. In particular, the mean area, the standard deviation and the product of the mean area and the standard deviation are preferable as a quantified value of the visual evaluation.

In the fourth aspect of the present invention, the inspection object is paper, and the degree of printing unevenness of printed portions on the paper is determined by the image processing.

In the fifth aspect of the present invention, the measurement of the printing unevenness of the gloss tone coated paper, mat tone coated paper and paperboard becomes possible. A quantified value is preferable to represent the degree of printing unevenness in halftone areas of the inspection object. Above all, it is preferable that the dark regions be detected as regions representing the printing unevenness in the gloss tone coated paper, mat tone coated paper and paperboard In the sixth aspect of the present invention, in addition to any one of the first, third, and fourth aspects of the present invention, the accuracy of measurement of printing unevenness is increased by emphasizing the brightness and darkness of the acquired image.

In the seventh aspect of the present invention, the measured result of printing is obtained by calculating the image areas of either the bright or dark portions which form the closed regions.

In the eighth aspect of the present invention, besides the seventh aspect of the present invention, transmitting only the diffused reflected light to the image pickup device can increase the accuracy of measurement of printing unevenness. This is because the inspection of the printing unevenness is carried out by observing the ink density, or more precisely, the unevenness of dot density, which depends on the diffused reflected light from the surface of the printed paper. Incidentally, the fine gloss irregularities of the coated paper are due to the regularly reflected light. Thus, this differs from the gloss irregularity due to the diffused reflected light, which causes the printing unevenness.

In the ninth aspect of the present invention, the accuracy of measurement of the gloss irregularity is increased by expressing the degree of the gloss irregularity by the product of the mean area and the standard deviation of the areas of the closed regions derived from the acquired image. It is preferable to adopt the mean area, the standard deviation and the product of the mean area and the standard deviation as a quantified value corresponding to the visually observed result of the gloss irregularity.

In the tenth aspect of the present invention, the inspection object is the mat paper, and the desirable accuracy of the measurement of the gloss irregularity of the mat paper is obtained by calculating the areas of the bright portions forming the closed regions.

In the eleventh aspect of the present invention, the object of inspection is the paperboard, and the desirable accuracy of measurement of the gloss irregularity on the paperboard is obtained by calculating the areas of the dark portions forming the closed regions. It is preferable with the gloss tone coated paper and paperboard to detect the dark portions as regions representing gloss irregularity, whereas with the mat coated paper, the bright portions.

In the twelfth aspect of the present invention, besides the tenth or eleventh aspect of the present invention, the accuracy of measurement of the gloss irregularity is increased by expressing the degree of the gloss irregularity by the mean area, or the standard deviation of the areas.

In the thirteenth aspect of the present invention, the accuracy of measurement of the gloss irregularity is increased by selecting the data of the closed regions of either the bright portions or the dark portions in accordance with the kind of paper.

In the fourteenth aspect of the present invention, besides the thirteenth aspect of the present invention, the measurement of the gloss irregularity is possible with the gloss tone coated paper, mat tone coated paper and paperboard.

In the fifteenth aspect of the present invention, besides the fourteenth aspect of the present invention, the accuracy of measurement of the gloss irregularity is increased by using the image data of the closed regions in the dark portions for the gloss tone coated paper.

In the sixteenth aspect of the present invention, besides the fourteenth aspect of the present invention, the accuracy of measurement of the gloss irregularity is increased by using the image data of the closed regions in the bright portions for the mat tone coated paper.

In the seventeenth aspect of the present invention, besides the fifteenth aspect of the present invention, the accuracy of measurement of the gloss irregularity is increased by using the image data of the closed regions in the dark portions for the paperboard.

In the eighteenth aspect of the present invention, besides any one of the ninth, tenth and eleventh aspect of the present invention, the accuracy of measurement of the gloss irregularity is increased by emphasizing the brightness and darkness of the acquired image.

BRIEF DESCRIPTION OF THE DRAWINGS

The accompanying drawings, which constitutes a part of the specification, show preferred embodiments of the present invention together with the specification, and will serve to understand the present invention by referring while reading the summary and the detailed description of the preferred embodiments.

BEST MODE FOR CARRYING OUT THE INVENTION

The embodiments of the present invention will now be described with reference to the accompanying drawings.

Figure 1:
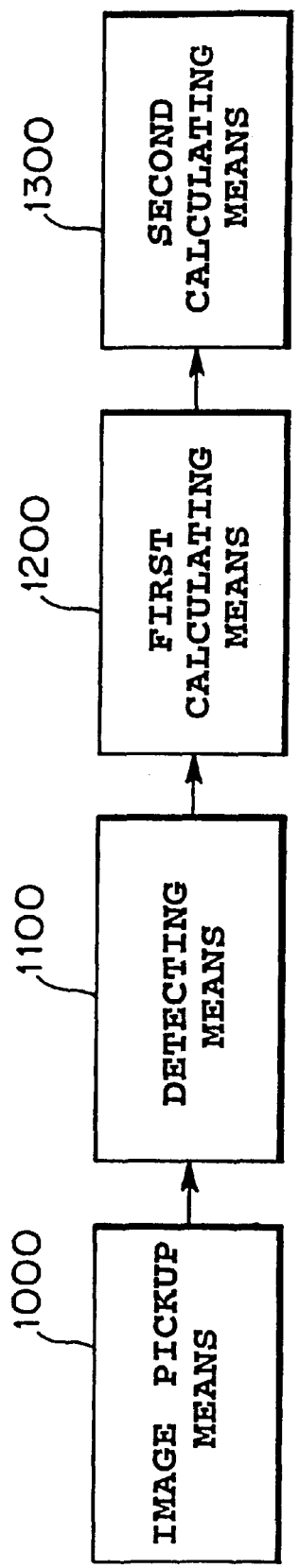
FIG. 1 is a functional structural diagram showing a fundamental arrangement of an embodiment in accordance with the present invention.

FIG. 1 shows a fundamental structure of an embodiment in accordance with the present invention.

In FIG. 1, the reference numeral 1000 designates a camera for acquiring an image of an inspected object.

The reference numeral 1100 designates a detecting means for detecting closed regions from the acquired image as gloss irregular regions and unevenly printed regions of the inspected object.

The reference numeral 1200 designates a first calculating means for calculating each area of the detected closed regions.

The reference numeral 1300 designates a second calculating means for calculating each distribution of calculated areas, and for outputting the calculated results as the measured results of gloss irregularity and printing unevenness.

Incidentally, the function of the detecting means 1100, and the first and second calculating means 1200 and 1300 is implemented with the calculation function of an image analyzer as will be described later.

Figure 2:
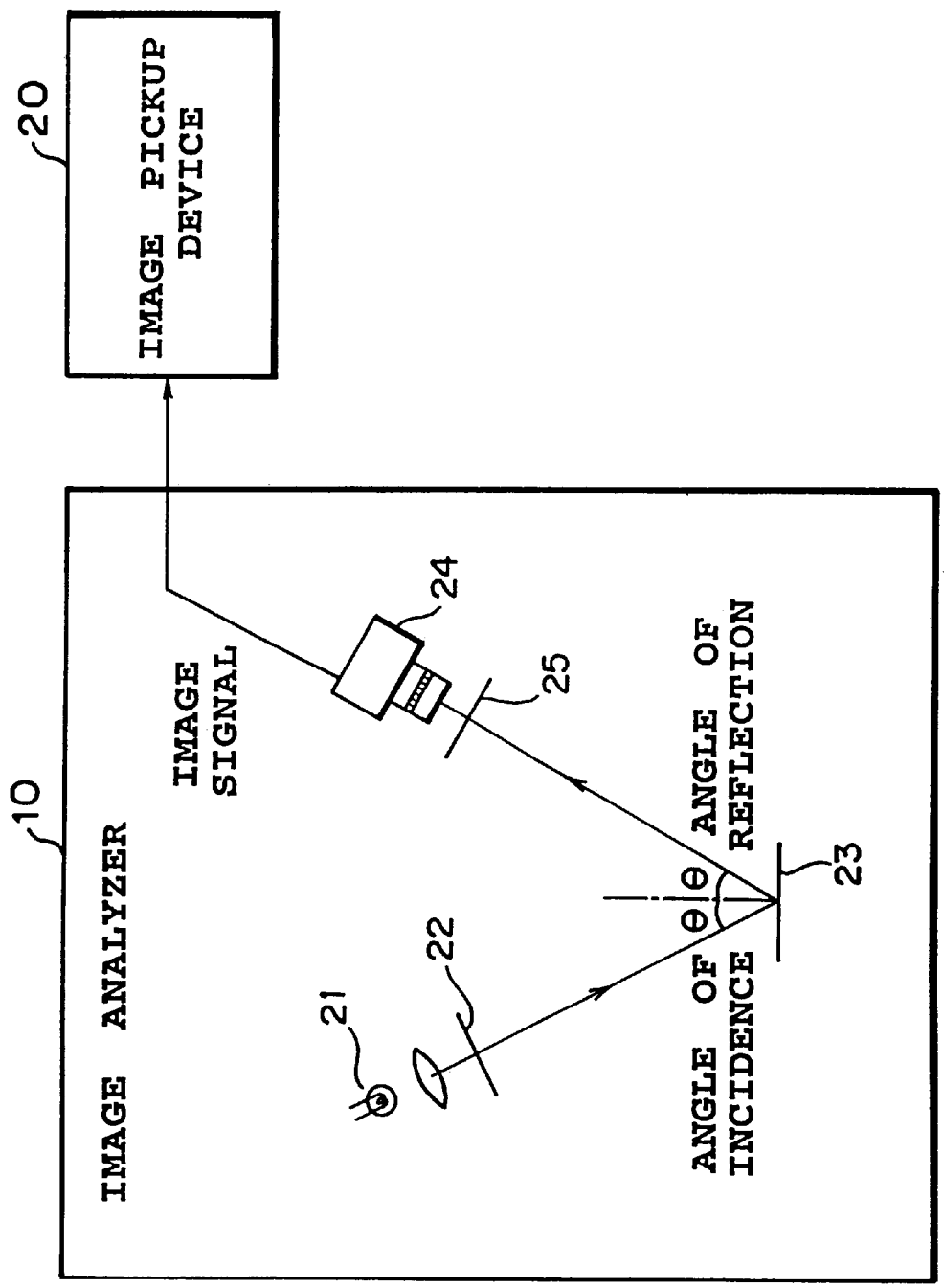
FIG. 2 is a structural diagram showing a structure of a first embodiment in accordance the present invention; A

FIG. 2 shows a schematic structure of a gloss irregularity measuring apparatus, to which the present invention is applied.

In FIG. 2, an inspection object 23 is irradiated with light projected from a light source 21 in an image pickup device (the acquisition means 1100 in FIG. 1) through a polarization filter 22. The light reflected from the object 23 is received by the TV camera 24 through a polarization filter 25. The TV camera 24 converts the received light into image signals pixel by pixel, thereby outputting them to an image analyzer 20.

It is preferable for the light source 21 to employ visible monochromatic light or white light in this embodiment. In addition, collimated or nearly collimated light is preferable as the incident light onto the surface of the object 23. Otherwise, it sometimes becomes difficult to catch the gloss irregularity because it spreads all over the image. The preferable angle of incidence is between 15 and 35 degrees, although not restricted within this range.

In this embodiment, it is preferable that the TV camera 24 acquire reflected light with an angle of reflection between −10−+10 degrees with the above angle of incidence. Out of this range, it becomes difficult to acquire the regular reflected light constituting the main gloss.

Passing the incident and reflected light through the polarization filters 22 and 25 makes it possible to cut off the diffused reflected light, and to transmit the regularly reflected light, thereby emphasizing the gloss irregularity.

The TV camera 24 used in this embodiment refers to a device for acquiring two dimensional (plane) image of the object 23, and any device can be employed as long as it acquires changes of brightness and darkness in a plane in terms of an electric signal. Although CCD cameras or video cameras, etc. are available on the market, a CCD camera is suitable for use because it has a linear relation between the brightness and the electric signal. It is preferable to set the focal length of the TV camera such that the resolution measured on the surface of the object becomes 0.5 mm or less, and the measured area of the object corresponding to the entire image becomes 2×2 mm$^2$ or more.

One of the distinguished features of the present invention is the analyzing method of the image signal, and the image analyzing processing will now be described.

An image signal associated with an image plane obtained by the TV camera 24, that is, luminance values (in gradation expression) of individual pixels are stored in a memory of the image analyzer 20. The image signal is then read by a CPU, and undergoes image analysis in the following processing steps.

(1) Fourier transform of the two-dimensional image is performed.

$$F(\omega) = \frac{1}{2\pi} \int_{-\infty}^{\infty} \int_{-\infty}^{\infty} e^{-i\omega x} f(x) dx \qquad [1]$$

$$\omega = \omega_x, \omega_y$$
$$x = x_x, x_y$$
$$dx = dx_x, dx_y$$

The result of the Fourier transform shows the power distribution of respective frequency bands, which is called power spectrum.

(2) An emphasized image is obtained, in which the brightness and darkness of the two-dimensional acquired image is emphasized, by multiplying by an emphasizing coefficient sections corresponding to particular frequencies perceivable by naked eyes while carrying out the inverse Fourier transform of the results of the Fourier transform. The inverse Fourier transform is expressed by the following expression.

$$f_1(x) = \frac{1}{2\pi} \left\{ \int_{-\infty}^{\omega} \int_{-\infty}^{\omega_1} e^{i\omega x} F(\omega) d\omega + \right.$$
$$\left. a \int_{\omega_1}^{\omega_2} \int_{\omega_1}^{\omega_2} e^{i\omega x} F(\omega) d\omega + \int_{\omega_2}^{\infty} \int_{\omega_2}^{\infty} e^{i\omega x} F(\omega) d\omega \right\} \quad [2]$$

where $\omega_1$ is an internal frequency, $\omega_2$ is an external frequency, a is an emphasizing coefficient, and $d\omega=d\omega_x$, $d\omega_y$.

(3) Decision parameters of the gloss irregularity are calculated as follows: Closed regions, which are formed by white portions corresponding to bright regions and by black portions corresponding to dark regions in the emphasized image, are detected as gloss irregular regions; the areas of individual detected closed regions, the average of the areas, the standard deviation of the areas, the coefficient of variation of the areas, or the number of white or black portions per unit area is calculated; and the calculated values are adopted as the decision parameters of the gloss irregularity corresponding to the inspection evaluation. These parameters express the degree of gloss irregularity (distribution) quantitatively.

In this context, the white portions and black portions refer to independent closed regions in an image which have gradations corresponding to white and black colors.

For reference, expressions for calculating the above-mentioned parameters will be shown below. It is needless to say that the image analyzer for this processing is operated as the detecting means 1100, the first calculating means 1200, and the second calculating means 1300 in FIG. 1.

$$\text{Mean: } S_M = \frac{\sum_{i=1}^{n} S_i}{n} \quad [3]$$

where Si is the area of i-th white or black portion, and n is the number of samples.

$$\text{Standard deviation: } S_\sigma = \sqrt{\frac{\sum_{i=1}^{n}(S_i - S_M)^2}{n}} \quad [4]$$

$$\text{Coefficient of variation: } S_V = \frac{S_\sigma}{S_M} \quad [5]$$

The number of samples is the number of white or black portions in the emphasized image divided by the surface area of the object converted into the image (the unit is $cm^2$), that is, the number of samples per unit area.

It is preferable that the particular wavelength range have a lower limit of 0.004–2.0 mm, and an upper limit of 2.0–200 mm. If the lower limit is set out of the range 0.004–2.0 mm, it deviates from the resolution of human eyes, and hence no effective measured values can be obtained. If the upper limit is set out of the range 2.0–200 mm, it falls beyond the range of human discrimination power, and hence no effective measured values can be obtained.

The emphasizing coefficient in expression (2) is preferable to be set at 2–50. No bipolarization of brightness and darkness is obtained if it is less than 2, and the form of irregular portions does not coincide with that of visual observation if it is beyond 50, so that no effective measured values can be obtained.

When the above calculation is processed by a computer, two-dimensional image is divided into a pixel assembly, and the gradation of individual pixels is input after digitization.

In the above-mentioned image analysis and processing, the operation for obtaining the white portions and black portions by the Fourier transform and inverse Fourier transform of the two-dimensional image can replace the conventional method in which the regions are determined using a rather arbitrary value called a "threshold". Since the operation in accordance with the present invention can set the same conditions for all the samples, highly reproducible and reliable measured values can be obtained.

The present method and apparatus for quantitatively measuring the gloss irregularity of inspected objects can preferably replace the conventional method which employs visual decision of the gloss irregularity of the surfaces of products. Since the present method does not require arbitrary operation, the result does not depend on the experience and judgement of inspectors, thereby providing the feature that the highly reproducible and reliable quantitative values are easily obtained.

Thus, the present invention offers a useful method and apparatus for measuring fine gloss irregularities not only of the plain surface or printed surface of coated paper, but also those of products which demand beautiful appearance and smoothness such as formed plastic surfaces, various application surfaces, and other surfaces.

Actually measured results of the gloss irregularity will be presented for reference. As coated paper samples, commercially available gloss tone high quality coated paper for sheet offset (33 samples of five groups from four types of A0–A3) was inspected.

The measuring apparatus shown in FIG. 2 was used for measuring the fine gloss irregularities of white paper. White visible collimated light (produced by a light projection apparatus HT-2 of Nikon) is polarized, and was projected on the surface of coated paper at 25 degrees of incidence relative to the normal. The reflected light at 25 degrees with respect to the normal was caused to pass through a polarization filter with the same phase as that of the incident light, and was detected by a CCD camera (CE 75 of SONY).

The acquired area of the surface of the object per pixel was 40×40 $\mu$m, and the measured area was 10×10 mm. Four data points per sample were picked up and the arithmetic mean was adopted.

The brightness of each pixel was converted into digital gradation by an A/D converter. The gradation from black to white was equally divided into 256 levels. The level of black was 0, and that of white was 255. The amount of light was set such that the gradation level of the brightest sample of respective groups of coated paper did not reach the level 255.

Figure 3A:
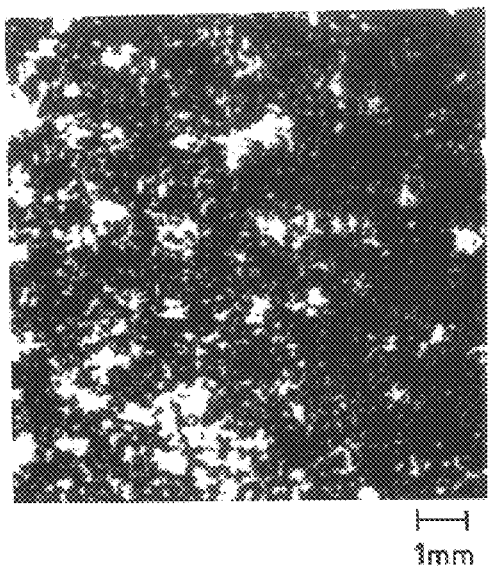
FIGS. 3a and 3b are image examples of acquired results and emphasis processing.
Figure 3B:
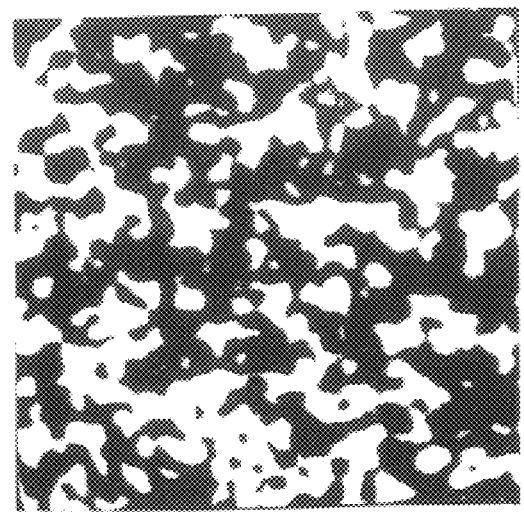

As for the condition of the image analysis (by image analyzer IP-1000: Asahi Chem. Ind.), the gloss irregularities are emphasized by carrying out the two-dimensional Fourier transform on the original image, and by multiplying the particular wavelength range visible to the naked eyes by the emphasizing coefficient The images before and after the emphasis are shown in FIG. 3. In the gradation of the image with its unevenness emphasized, the range 0–1 was termed "black portion", and the range 254–255 was termed "white portion".

After individual areas of black portions (dark portions in the original image) and white portions (bright portions in the original image) were calculated, the standard deviations of the areas were calculated.

As for the visual ranking, seven to eighteen specialists in and out of our company who had been engaged in the evaluation of paper qualities-decided the rank orders, and their arithmetic means were adopted as the mean rank order of visual inspection. The rank order was represented by the integers as 1, 2, 3, . . . in descending order of surface feeling in each group.

Figure 4:
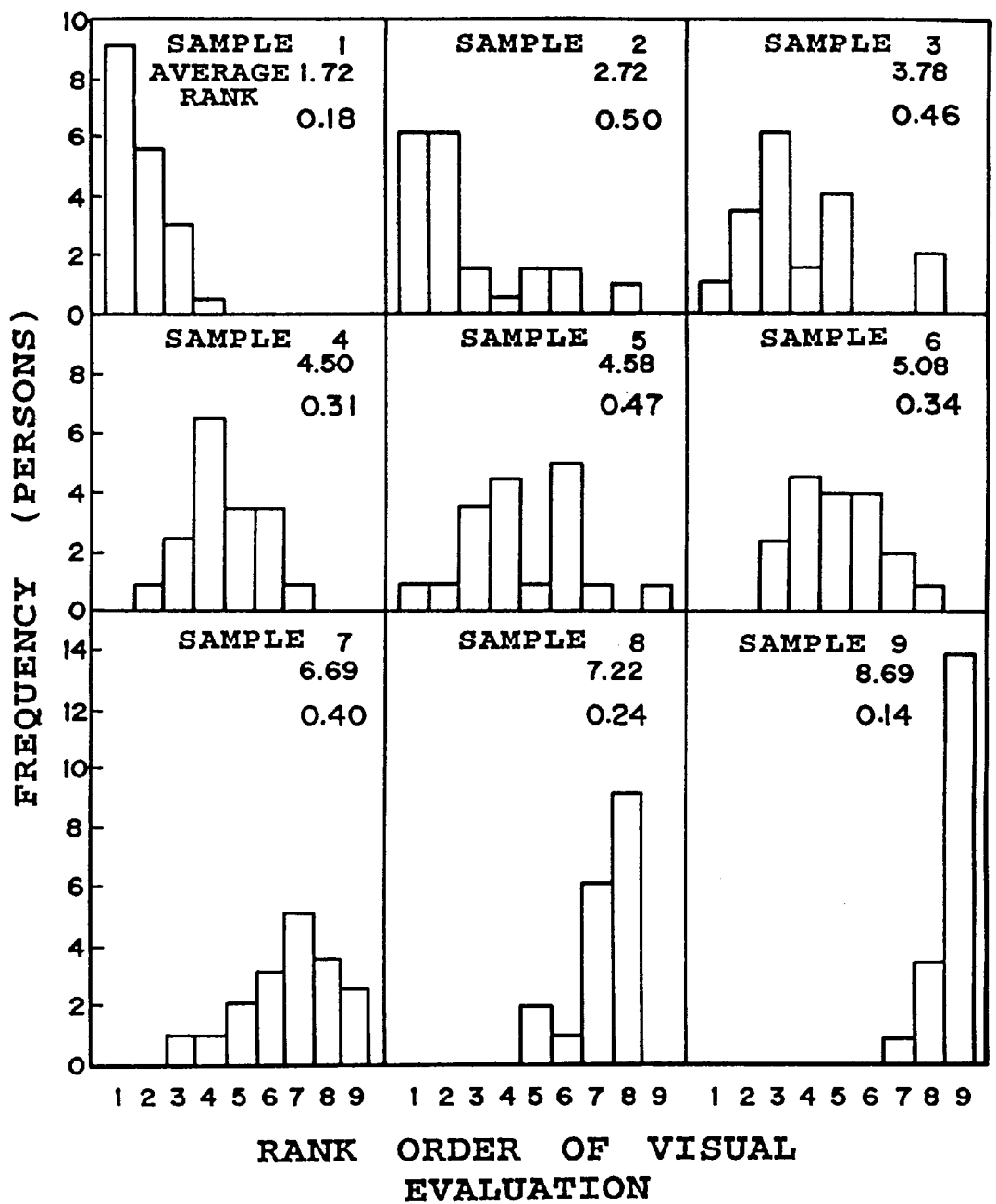
FIG. 4 is diagrams showing measured and evaluated results by visual inspection.
Figure 5:
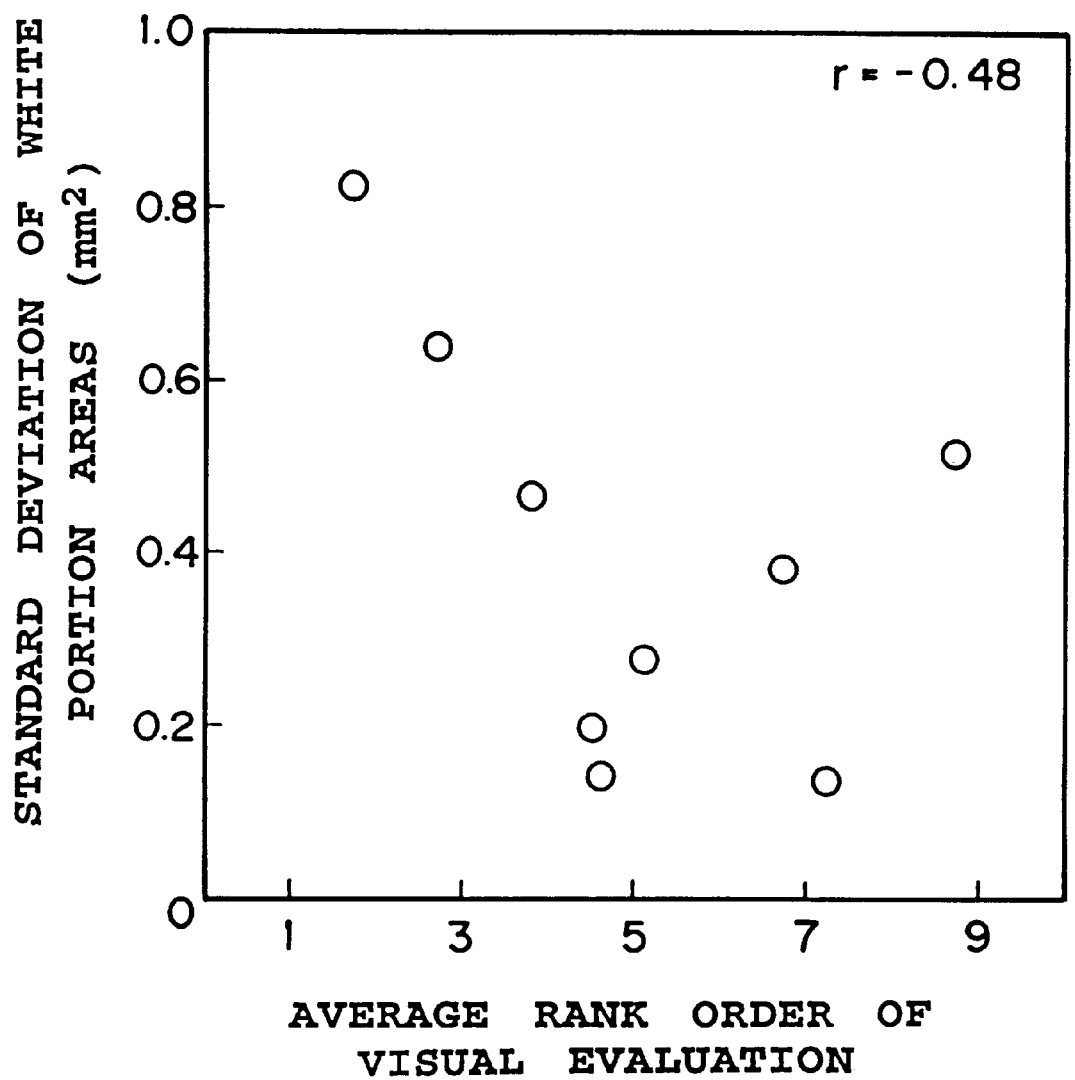
FIG. 5 is a diagram illustrating relations between the mean rank order of visual inspection and the standard deviation of bright areas associated with gloss irregularity.
Figure 6:
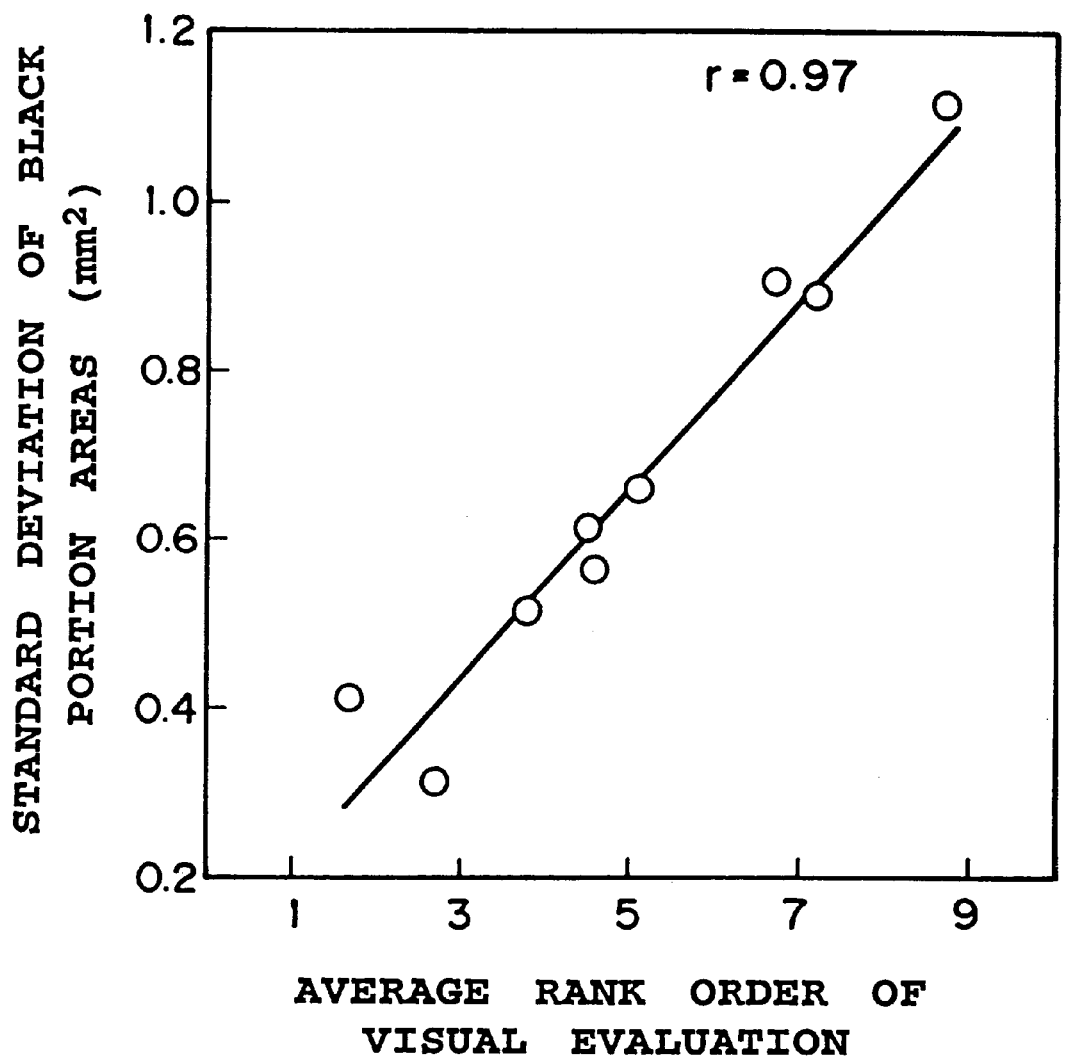
FIG. 6 is a diagram illustrating relations between the mean rank order of visual inspection and the standard deviation of dark areas associated with gloss irregularity.
Figure 7:
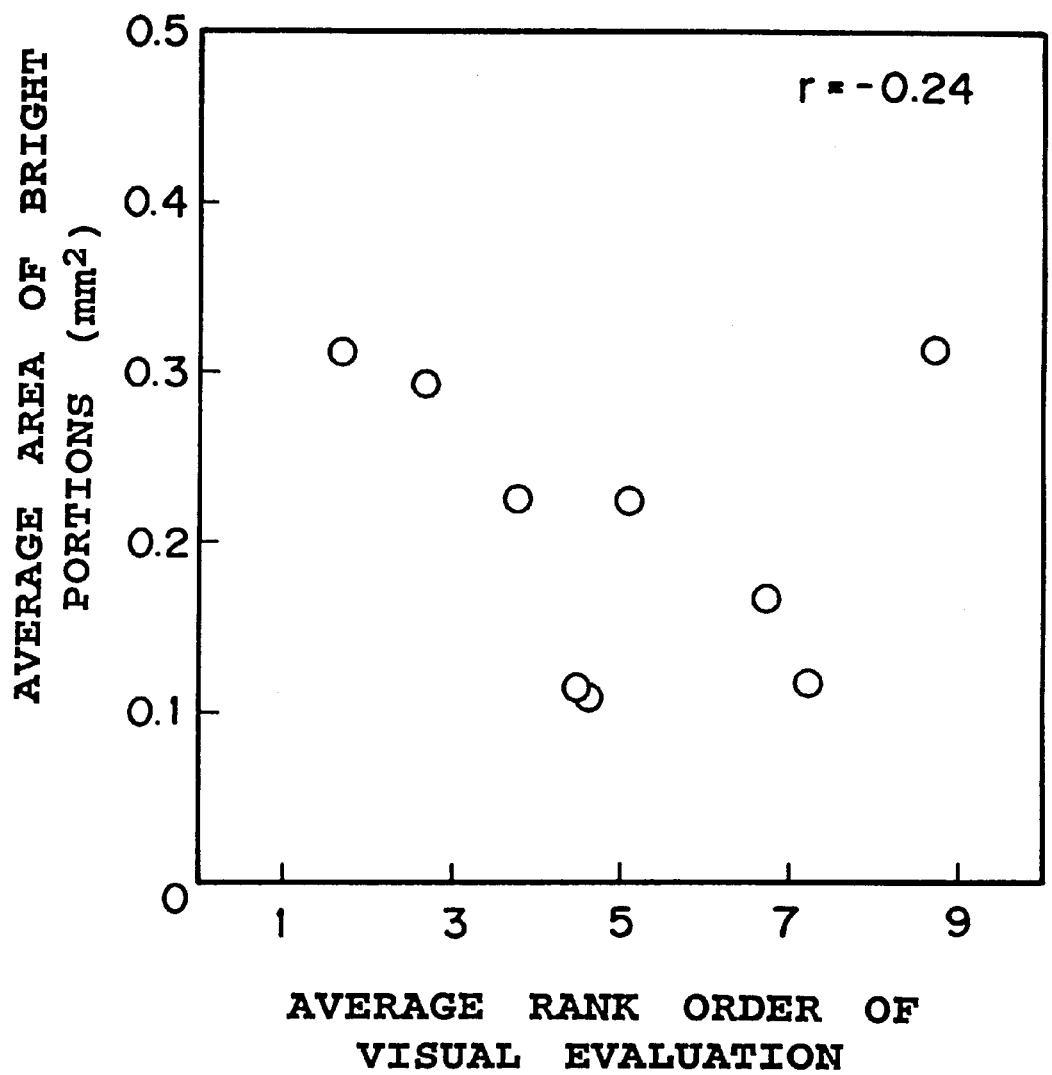
FIG. 7 is a diagram illustrating relations between the mean rank order of visual inspection and the mean areas of bright regions associated with gloss irregularity.
Figure 8:
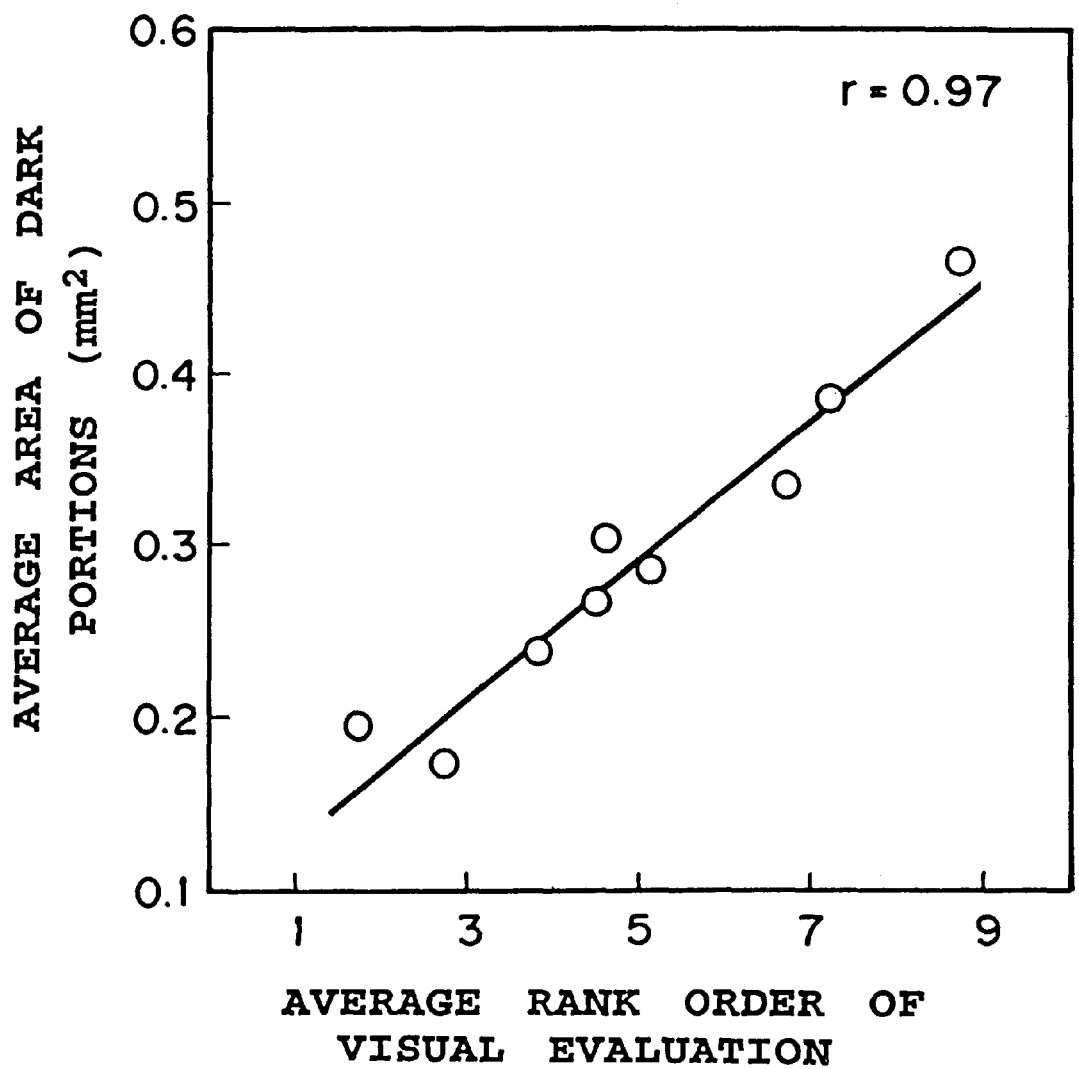
FIG. 8 is a diagram illustrating relations between the mean rank order of visual inspection and the mean areas of dark regions associated with gloss irregularity.
Figure 9:
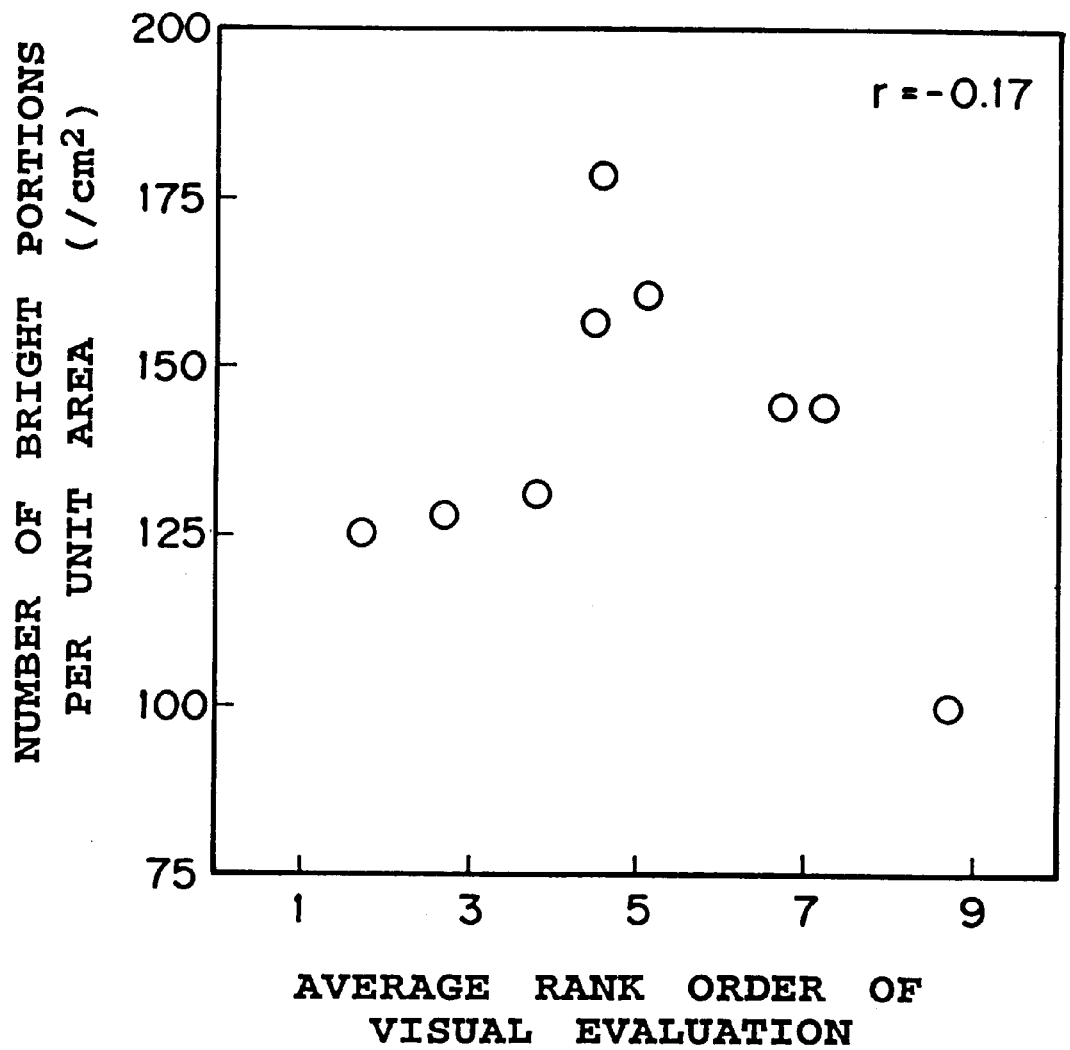
FIG. 9 is a diagram illustrating relations between the mean rank order of visual inspection and the density of bright regions associated with gloss irregularity.
Figure 10:
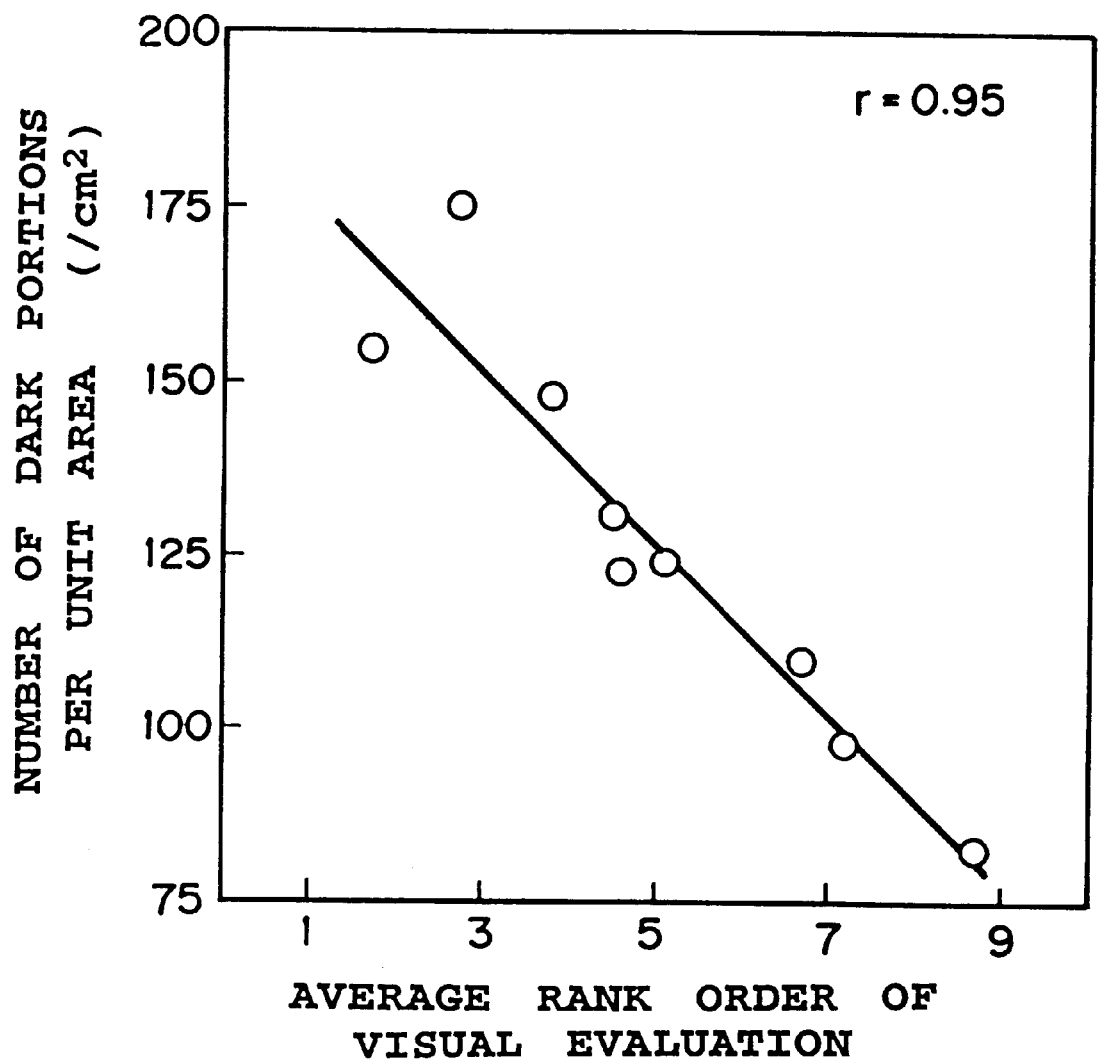
FIG. 10 is a diagram illustrating relations between the mean rank order of visual inspection and the density of dark regions associated with gloss irregularity.

The rank orders of visual evaluation of marketed A2 gloss papers (79 g/m²) by 18 inspectors are shown in FIG. 4. FIGS. 5 and 6 show the relations between the mean visual rank orders and the standard deviations of emphasized white and black portions which correspond to the gloss irregularity of the coated papers. The emphasized wavelength range in this case was 0.4–8.0 mm, and the emphasizing coefficient The mean areas of black portions and the standard deviations of other kinds of marketed gloss paper for sheet offset were determined with the same measuring method, and the correlation coefficients were calculated between these values and the mean rank orders of visual evaluation. The results are shown in the following Table 1. The correlation coefficients of the standard deviations were 0.90–0.97, which shows good correlations. The correlation coefficients associated with the mean area of black portions were 0.89–0.97, which also shows good correlations. However, the correlation coefficients associated with the standard deviation showed rather higher values.

TABLE 1

Gloss values of sub-millimeter region on the white coated paper

| Type | A0 | A1 | A2 | A2 | A3 |
|---|---|---|---|---|---|
| Basis weight (g/m²) | 128 | 128 | 128 | 79 | 70 |
| Number of samples | 5 | 7 | 5 | 9 | 7 |
| 75° gloss of white paper (%) | 76–83 | 72–78 | 60–67 | 56–71 | 47–59 |
| Correlation coefficients | | | | | |
| with the standard deviation of black portion areas | 0.96 | 0.90 | 0.95 | 0.97 | 0.94 |
| with the average areas of black portions | 0.97 | 0.90 | 0.97 | 0.97 | 0.84 |
| Range | | | | | |
| the standard deviation of black portions (mm²) | 0.21–0.57 | 0.24–0.56 | 0.30–0.79 | 0.31–1.10 | 0.46–0.76 |
| the average areas of black portions (mm²) | 0.10–0.20 | 0.12–0.26 | 0.18–0.32 | 0.17–0.46 | 0.23–0.32 |
| The average gradation of the two-dimensional images | 83–135 | 77–118 | 77–123 | 74–149 | 69–115 | was 10, As shown in FIGS. 5 and 6, the correlation coefficient of the white portions was r=0.48, and that of the black portions was r=0.97. In this connection, the correlation coefficient between the mean rank order of visual evaluation and the coefficient of variation of the gradation was r=0.72, and the-correlation coefficient between the mean rank order of visual evaluation and the standard deviation of gradation was r=−0.35. From these results, it is seen that the visual evaluation of gloss paper are carried out by observing dark portions rather than bright portions of the gloss irregularities. Furthermore, it would be considered that the standard deviation of the areas of black portions rather than the parameters representing gradation is the controlling factor to visual perception.

The relation between the mean rank order of visual evaluation and the mean area per one white or black portion, and the relation between that rank order and the number of white or black portions per unit area are shown in FIGS. 7 to 10. Very good correlations were obtained between the mean value of the dark portions and the visual evaluation, and between the number of black portions per unit area and the visual evaluation.

Figure 11:
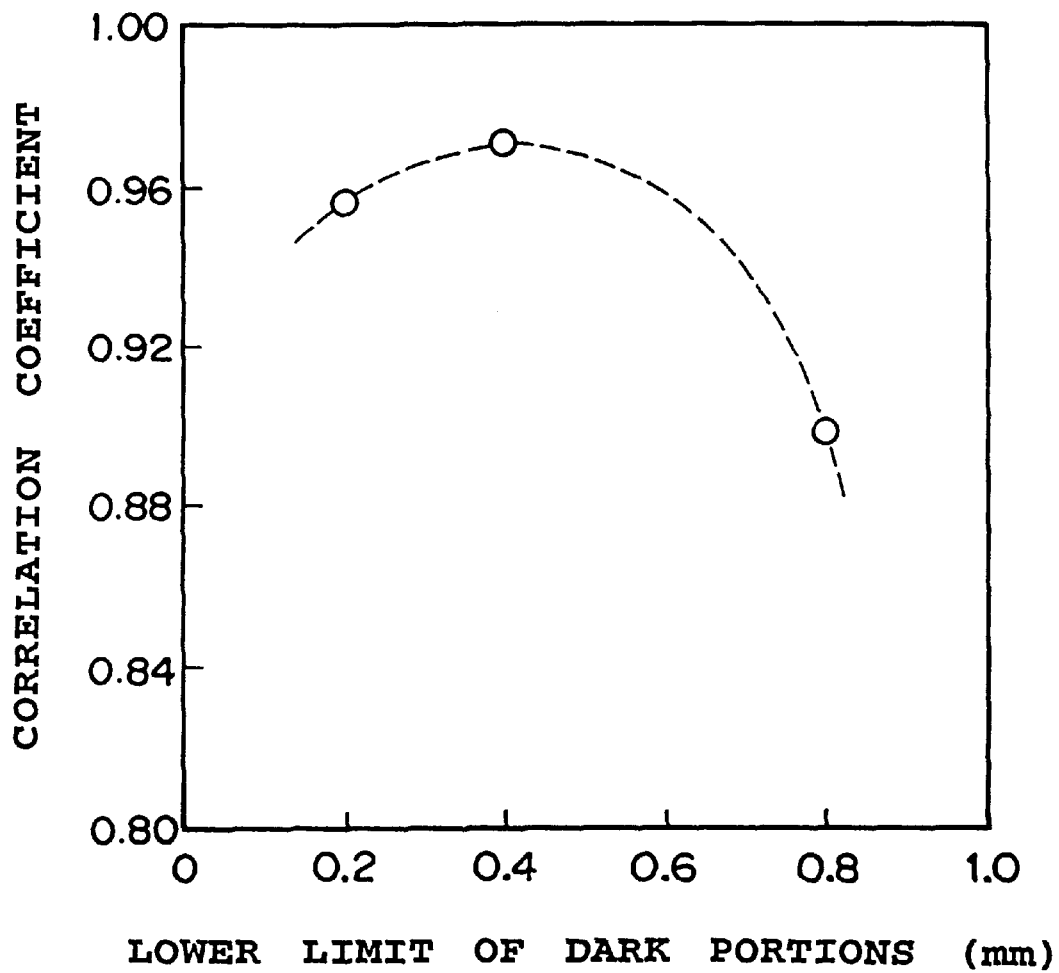
FIG. 11 is a diagram illustrating relations between the lower limit of the areas of dark regions and correlation coefficients (between the mean of visual inspection and the standard deviation of the areas of the dark regions) in Fourier transform.
Figure 12:
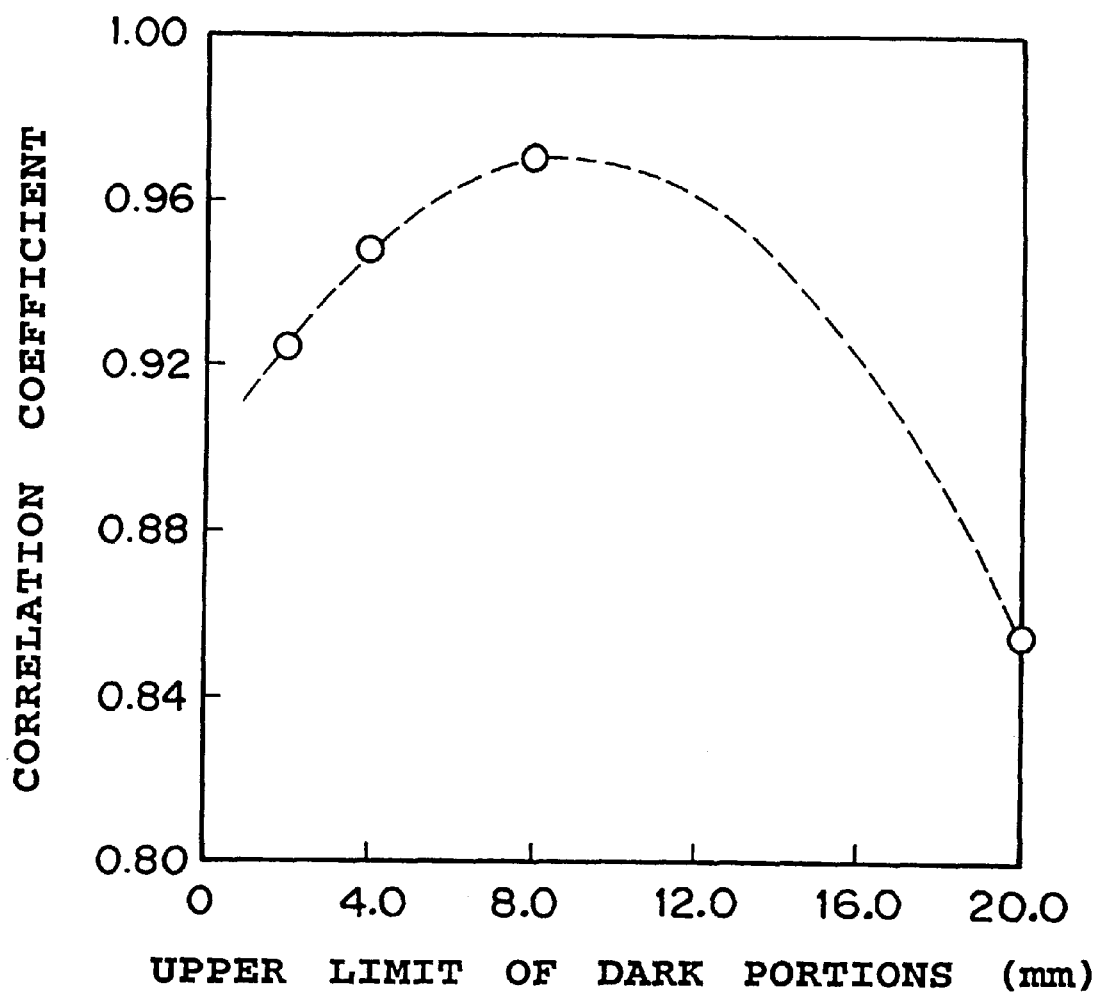
FIG. 12 is a diagram illustrating relations between the upper limit of the areas of dark regions and correlation coefficients (between the mean of visual inspection and the standard deviation of the areas of the dark regions) in Fourier transform.
Figure 13:
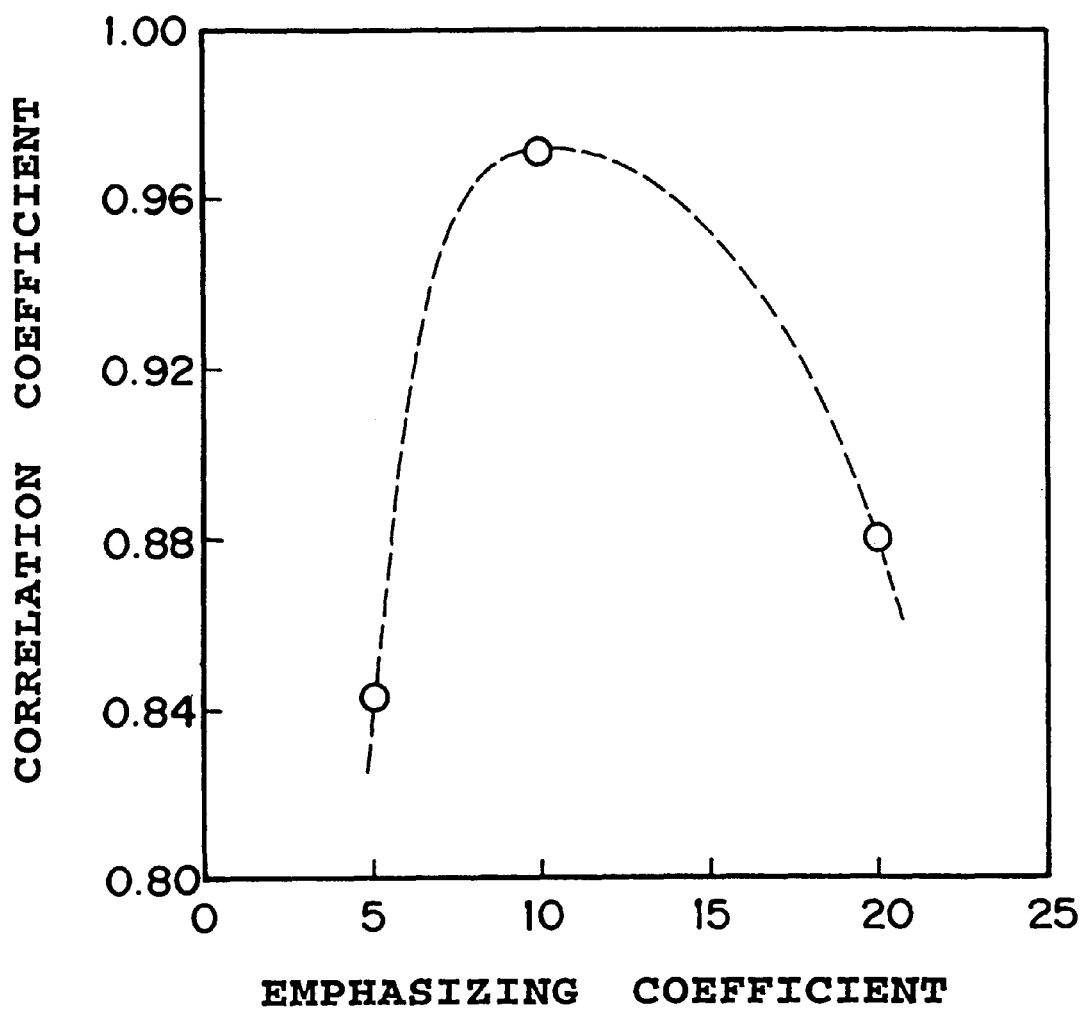
FIG. 13 is a diagram illustrating relations between emphasis coefficients and correlation coefficients in Fourier transform.

A trial was made to specify the boundary conditions of the emphasizing range in the inverse Fourier transform. FIG. 11 shows the relationships between the correlation coefficient and the lower limit of the range, and FIG. 12 shows the relationships between the correlation coefficient and the upper limit of the range. From these two figures, it can be concluded that the optimum wavelength range of the emphasis falls between 0.4 and 8.0 mm. Furthermore, the examination in that range with an emphasizing coefficient of 5 to 20 confirmed that 10 is best (FIG. 13).

Figure 14:
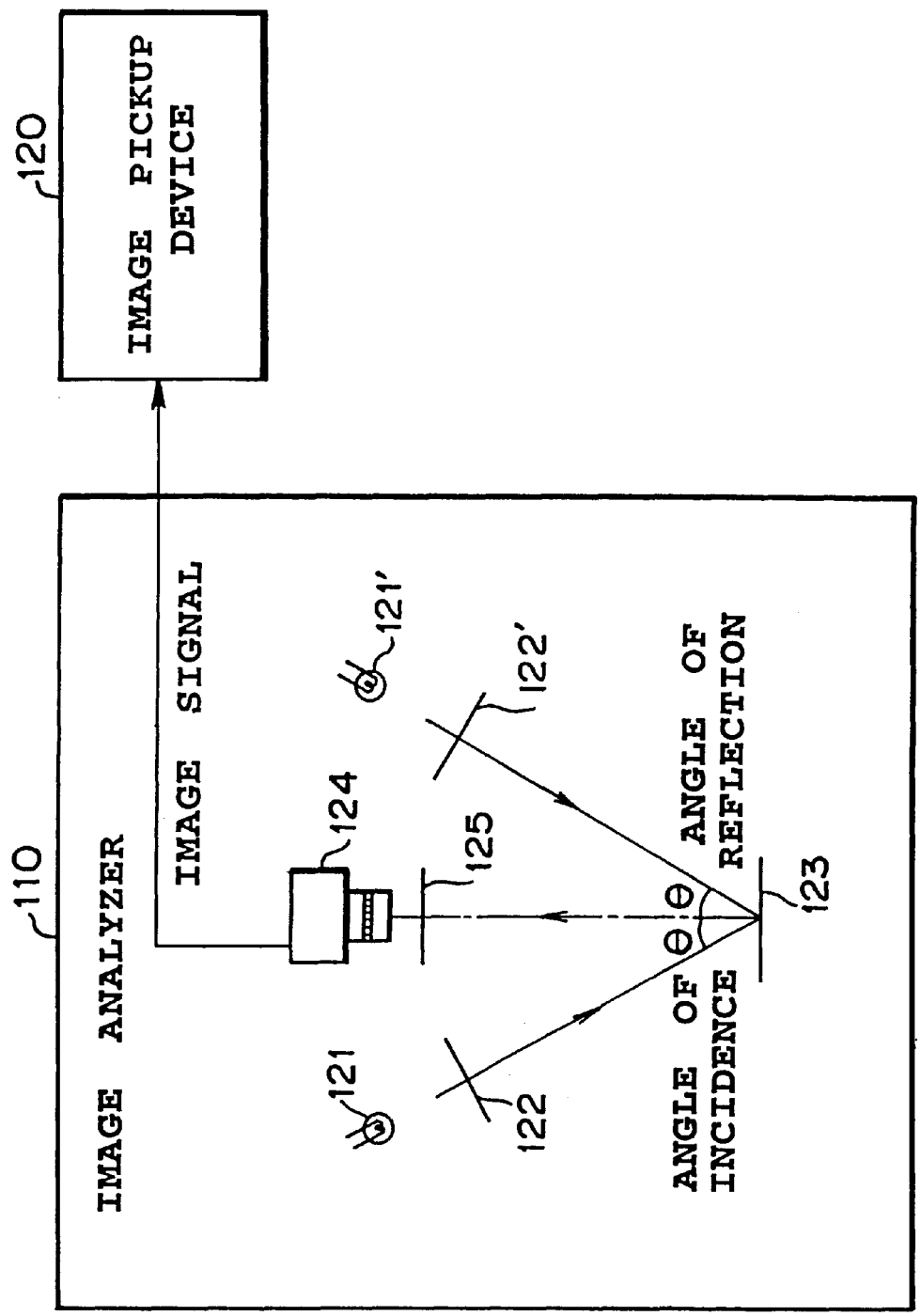
FIG. 14 is a block diagram showing the structure of a second embodiment.

FIG. 14 shows a schematic structure of a measuring apparatus in a second embodiment of the present invention.

In FIG. 14, light is projected onto an inspection object 123 from light sources 121 and 121' in the image pickup device 10 through polarization filters 122 and 122'.

The light reflected from the object 123 is received by a TV camera 124 through the polarization filter 125. The TV camera 124 converts the received light into image signals, pixel by pixel, and outputs them to an image analyzer 120.

It is preferable that the light source 121 of this embodiment use visible monochromatic light and white light. The light incident onto the surface of the object 123 may be either collimated or diffused light, and not specifically limited. In this embodiment, it is preferable that the TV camera 124 receive the diffused reflected light. The diffused reflected light is transmitted, but the regularly reflected light is cut off, when the reflected light passes through a polarization filter 125 whose phase differs by 90 degrees from that of the polarization filters 122 and 122' (which have the same phase) for the incident light. This will further emphasize the printing unevenness.

The TV camera 124 employed in this embodiment refers to a device for acquiring two-dimensional (plane) image of the object 123. Any device can be used as long as it can pick up changes of printing unevenness in the plane, thereby producing electric signals. Among the marketed products, there are CCD cameras and video cameras, but the CCD camera is preferable because it has the linear relation between the brightness and the electric signal. It is desirable to select the focal length of the TV camera so that the resolution falls below 0.5 mm in terms of the size on the surface of the object, and the measured area of the object corresponding to the whole image is more than 2×2 mm. The image analysis in this embodiment is performed by Fourier analysis using expression (1) as in the first embodiment. More specifically, the image signal associated with one plane acquired by the TV camera, namely, the luminance values (expressed in terms of gradation) for individual pixels are stored in the memory in the image analyzer 120. Then, they are read by the CPU to undergo the image analysis in the following steps.

(1) The two-dimensional image is Fourier transformed using expression (1).

The result of the Fourier transform shows the power distribution of respective frequency bands, and is called power spectrum (2) An emphasized image is obtained, in which the light and dark portions are emphasized in the acquired two-dimensional image, by multiplying the emphasizing coefficient by portions corresponding to the particular wavelength range that can be perceived by naked eyes, when the Fourier transformed image is inversely transformed using the above mentioned expression [2].

(3) Closed regions, which are formed by white portions corresponding to bright regions and by black portions corresponding to dark regions in the emphasized image, are detected as gloss irregular regions; the areas of individual detected closed regions, the average of the areas, the standard deviation of the areas, the coefficient of variation of the areas, or the number of white or black portions per unit area is calculated; and the calculated values are adopted as the decision parameters of the gloss irregularity corresponding to the inspection evaluation. These parameters express the degree of gloss irregularity (distribution) quantitatively.

In this context, the white portions and black portions refer to independent closed regions in an image which have gradations corresponding to white and black colors.

If the closed region has a narrow part, an operation may be added to separate the image at that part.

The above-mentioned expressions (3)–(5) are used to calculate the parameters. As for the special range of the wavelength, it is preferable that the particular wavelength range have a lower limit of 0.004–2.0 mm, and an upper limit of 2.0–200 mm. If the lower limit is set out of the range 0.004–2.0 mm, it deviates from the resolution of human eyes, and hence no effective measured values can be obtained. If the upper limit is set out of the range 2.0–200 mm, it falls beyond the range of human discrimination power, and hence no effective measured values can be obtained.

In the second embodiment, the emphasizing coefficient in expression (2) is preferable to be set at 2–500. No bipolarization of brightness and darkness is obtained if it is less than 2, and the form of irregular portions does not coincide with that of visual observation if it exceeds 500, so that no effective measured values can be obtained. A more preferable range is 30–300.

When the above calculation is processed by a computer, two-dimensional image is divided into a pixel assembly, and the gradation of individual pixels is input after digitization.

In the above-mentioned image analysis and processing, the operation for obtaining the white portions and black portions by the Fourier transform and inverse Fourier transform of the two-dimensional image can replace the conventional method in which the regions are determined using a rather arbitrary value called a "threshold" Since the operation in accordance with the present invention can set the same conditions for all the samples, highly reproducible and reliable measured values can be obtained.

The present method and apparatus for quantitatively measuring the printing unevenness of inspected objects can preferably replace the conventional method which employs visual decision of the printing unevenness of the surfaces of products. Since the present method does not require arbitrary operation, the result does not depend on the experience and judgement of inspectors, thereby providing the feature that the highly reproducible and reliable quantitative values are easily obtained.

Thus, the present invention offers a useful method and apparatus for quantitatively evaluate printing unevenness not only of the coated paper, but also those of products which demand printability of surfaces such as formed plastic surfaces, various application surfaces, and other surfaces.

Actually measured results of the printing unevenness will be presented for reference. The samples of printed coated paper were prepared as follows: First, commercially available A2 size gloss tone high quality coated paper for sheet offset (basis weight was 127.9 g/m$^2$, and 10 samples were used); Then, multicolored halftone portions were inspected which had been printed by a four-colored unit type printer.

The measuring apparatus shown in FIG. 14 was used for measuring the printing unevenness of the printed coated paper. White visible light is polarized, and was projected on the surface of the printed coated paper at 45 degrees of incidence relative to the normal. The reflected light at 0degree with respect to the normal was caused to pass through a polarization filter with a phase different by 90 degrees from that of the incident light, and was detected by a CCD camera (CE-75 of SONY).

The acquired area of the surface of the object per pixel was 100×100 μm, and the measured area was 25×25 mm. Four data points per sample were picked up and the arithmetic mean was adopted.

The brightness of each pixel was converted into digital gradation by an A/D converter. The gradation from black to white was equally divided into 256 levels. The level of black was 0, and that of white was 255. The amount of light was controlled such that the gradation levels of the samples of the printed coated paper did not reach the gradation level 255.

As for the condition of the image analysis (by image analyzer IP-1000: Asahi Chem. Ind.), the unevenness of the image is emphasized by carrying out the two-dimensional Fourier transform on the original image, and by multiplying the particular wavelength range visible to the naked eyes by the emphasizing coefficient. In the gradation of the image with its unevenness emphasized, the range 0–1 was termed "black portion", and the range 254–255 was termed "white portion". After individual areas of black portions (dark portions in the original image) and white portions (bright portions in the original image) were calculated, the mean area and the standard deviation of the areas were calculated.

As for the visual ranking, twelve specialists in and out of our company who had been engaged in the evaluation of paper qualities decided the rank orders, and their arithmetic means were adopted as the mean rank order of visual inspection. The rank order was represented by the integers as 1, 2, 3, . . . in descending order of the printing unevenness in each group.

Figure 15:
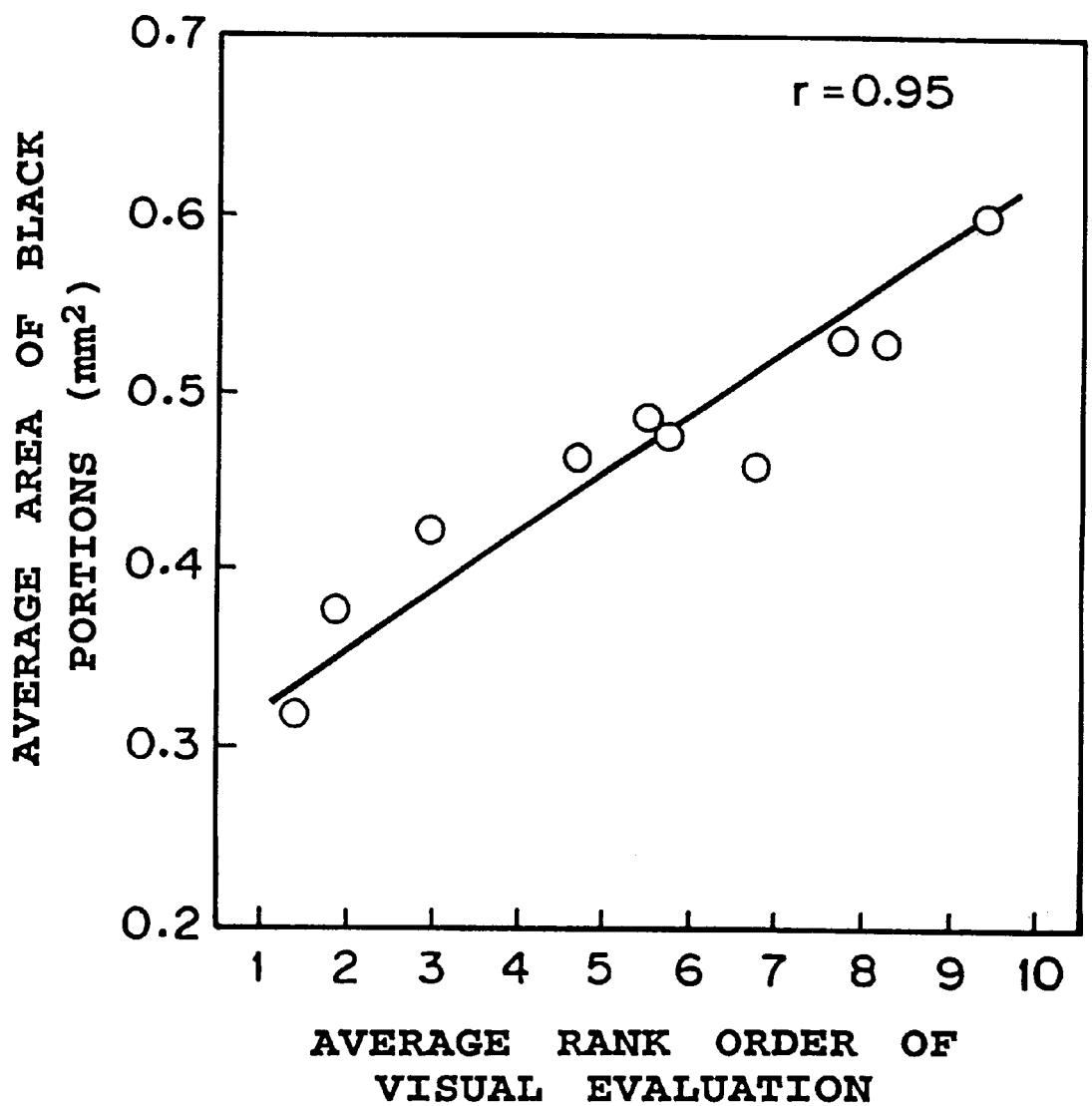
FIG. 15 is a diagram illustrating relations between the mean area of black regions and the mean rank order of visual inspection.
Figure 16:
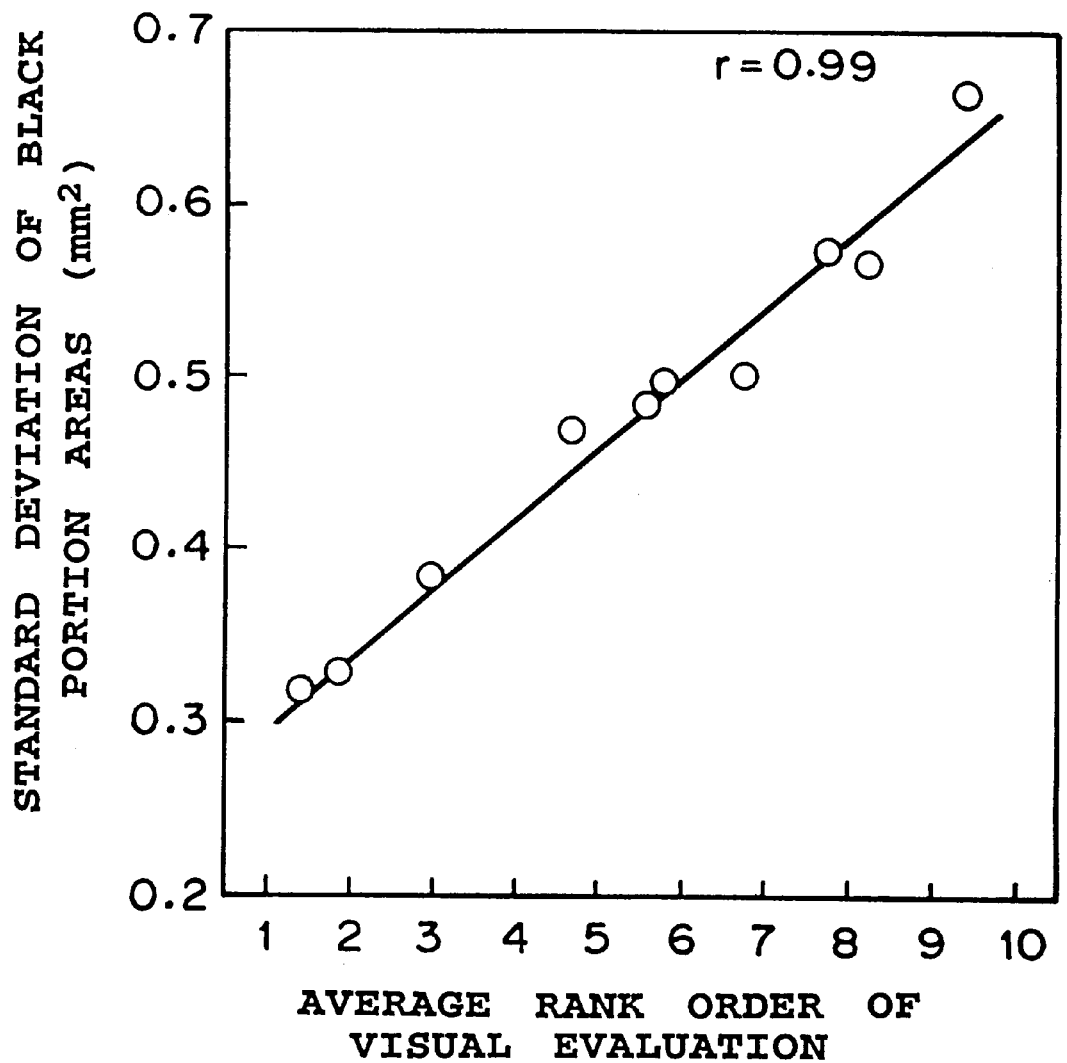
FIG. 16 is a diagram illustrating relations between the standard deviation of black regions and the mean rank order of visual inspection.

The rank orders of visual evaluation of the halftone portions by 12 inspectors are shown in Table 2, the halftone portions being printed in multicolor on marketed A2 gloss papers. FIG. 15 shows the relations between the mean rank order of visual evaluation and the mean areas of the emphasized black portions corresponding to the printing unevenness of the coated paper. In this case, the emphasized wavelength range in the inverse Fourier transform was 1.2 to 6.2 mm, and the emphasizing coefficient was 160. As clearly seen from FIG. 15, the correlation coefficient was r=0.95. FIG. 16 shows the relations between the mean rank orders of the visual evaluation and the standard deviations of the areas of the black portions. There is a very high correlation between the distribution of the areas of the black portions and the visual evaluation.

Similar measurements were carried out with the printed matters of marketed A0 to A3 size coated paper for sheet offset, in which the printing unevenness of the monochromatic halftone portions of Chinese black, indigo, or crimson was measured using an emphasized wavelength range of 0.8–4.0 mm, and an emphasizing coefficient of 80–240. Thus, the mean areas of the black portions and their standard deviations were obtained. The correlation coefficients between these values and the mean rank orders of the visual evaluation were calculated, and its results are shown in Tables 3–5.

TABLE 2

Visual evaluation of printing unevenness on coated paper (A2) halftone region of multicolor printing

| Sample | 1 | 2 | 3 | 4 | 5 | 6 | 7 | 8 | 9 | 10 |
|---|---|---|---|---|---|---|---|---|---|---|
| Mr. A | 1 | 9 | 3 | 2 | 4 | 8 | 7 | 6 | 5 | 10 |
| Mr. B | 1 | 7 | 3 | 2 | 5 | 8 | 6 | 9 | 4 | 10 |
| Mr. C | 1 | 8 | 3 | 2 | 4 | 9 | 7 | 5 | 6 | 10 |
| Mr. D | 2 | 7 | 5 | 1 | 4 | 10 | 9 | 3 | 8 | 8 |
| Mr. E | 1 | 7 | 3 | 2 | 5 | 9 | 8 | 6 | 4 | 10 |
| Mr. F | 1 | 6 | 3 | 2 | 5 | 8 | 9 | 7 | 4 | 10 |
| Mr. G | 2 | 8 | 1 | 3 | 7 | 5 | 9 | 4 | 8 | 10 |
| Mr. H | 2 | 5 | 3 | 1 | 4 | 9 | 8 | 6 | 7 | 10 |
| Mr. I | 3 | 4 | 1 | 2 | 9 | 7 | 6 | 5 | 8 | 10 |
| Mr. J | 1 | 8 | 4 | 2 | 3 | 7 | 9 | 6 | 4 | 10 |
| Mr. K | 1 | 7 | 3 | 2 | 4 | 10 | 8 | 6 | 5 | 9 |
| Mr. L | 1 | 6 | 4 | 2 | 3 | 10 | 8 | 7 | 5 | 9 |
| Average | 1.42 | 6.83 | 3.00 | 1.92 | 4.75 | 8.33 | 7.83 | 5.83 | 5.58 | 9.50 |

1–10 = good → bad

TABLE 3

Correlation between visual evaluation and measured values of printing unevenness (monochromatic Chinese black halftone portion)

| Type | A0 | A1 | A2 | A3 |
|---|---|---|---|---|
| Basis weight (g/m$^2$) | 127.9 | 127.9 | 79.1 | 79.1 |
| Number of samples | 6 | 5 | 9 | 8 |
| Correlation coefficients | | | | |
| with the average areas of black portions | 0.93 | 0.96 | 0.94 | 0.95 |
| with the standard deviations of the areas of black portions | 0.93 | 0.94 | 0.95 | 0.95 |
| Equivalent circle diameter of black portions (mm) | 0.44–0.54 | 0.43–0.59 | 0.52–0.65 | 0.54–0.62 |

TABLE 4

Correlation between visual evaluation and measured values of printing unevenness (monochromatic indigo halftone portion)

| Type | A0 | A1 | A2 | A3 |
|---|---|---|---|---|
| Basis weight (g/m$^2$) | 127.9 | 127.9 | 79.1 | 79.1 |
| Number of samples | 6 | 5 | 9 | 8 |
| Correlation coefficients | | | | |
| with the average areas of black portions | 0.97 | 0.97 | 0.92 | 0.94 |
| with the standard deviations of the areas of black portions | 0.93 | 0.88 | 0.90 | 0.93 |
| Equivalent circle diameter of black portions (mm) | 0.54–0.64 | 0.53–0.64 | 0.52–0.60 | 0.56–0.64 |

TABLE 5

Correlation between visual evaluation and measured values of printing unevenness
(monochromatic red halftone portion)

| Type | A0 | A1 | A2 | A3 |
|---|---|---|---|---|
| Basis weight (g/m$^2$) | 127.9 | 127.9 | 79.1 | 79.1 |
| Number of samples | 6 | 5 | 9 | 8 |
| Correlation coefficients | | | | |
| with the average areas of black portions | 0.89 | 0.97 | 0.94 | 0.93 |
| with the standard deviations of the areas of black portions | 0.80 | 0.94 | 0.92 | 0.92 |
| Equivalent circle diameter of black portions (mm) | 0.41–0.45 | 0.49–0.58 | 0.48–0.59 | 0.49–0.56 |

Figure 17:
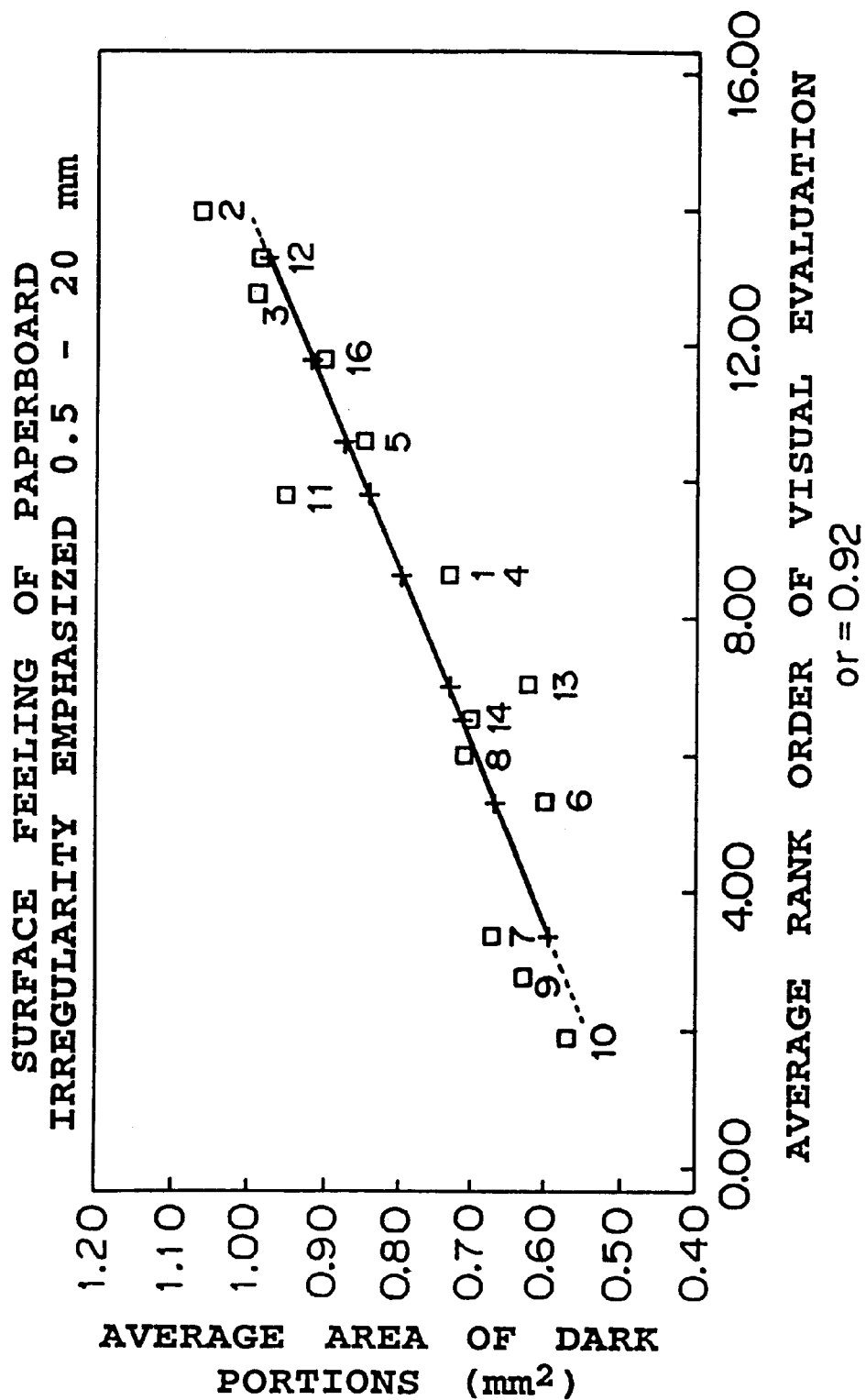
FIG. 17 is a diagram illustrating relations between the mean rank order of visual inspection and the mean area of dark regions.
Figure 18:
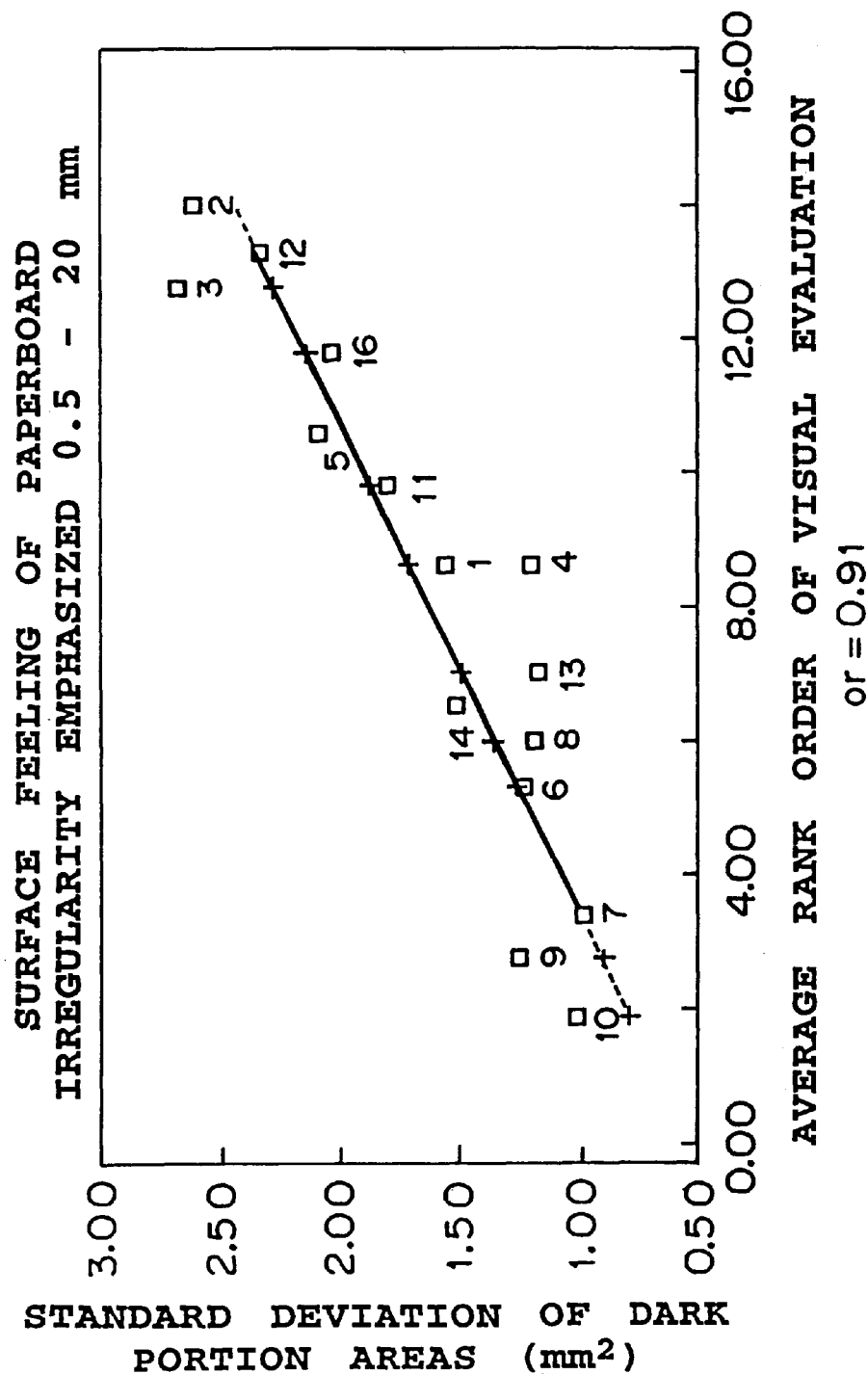
FIG. 18 is a diagram illustrating relations between the mean rank order of visual inspection and the standard deviation of dark regions.

The above mentioned measured results were obtained from the gloss tone coated paper with a high gloss value of about 45 to 85%. The present invention can be applied to other kinds of papers. For example, the present invention can be applied to a paperboard. FIG. 17 shows measured results thereof, that is, the relationships between the mean area of the black portions and the mean rank order of visual evaluation. FIG. 18 shows the relationships between the standard deviation of the black portion areas and the mean rank order of visual evaluation. Referring to FIGS. 17 and 18, it can be seen that there are correlations between the mean rank order of the visual evaluation and the mean area or the standard deviation of the dark areas. It is also shown that the data associated with the dark portions are preferable in the case of paperboard. In this case, the emphasized wavelength range was 0.5–20.0 mm, and the emphasizing coefficient was 10.

Figure 19:
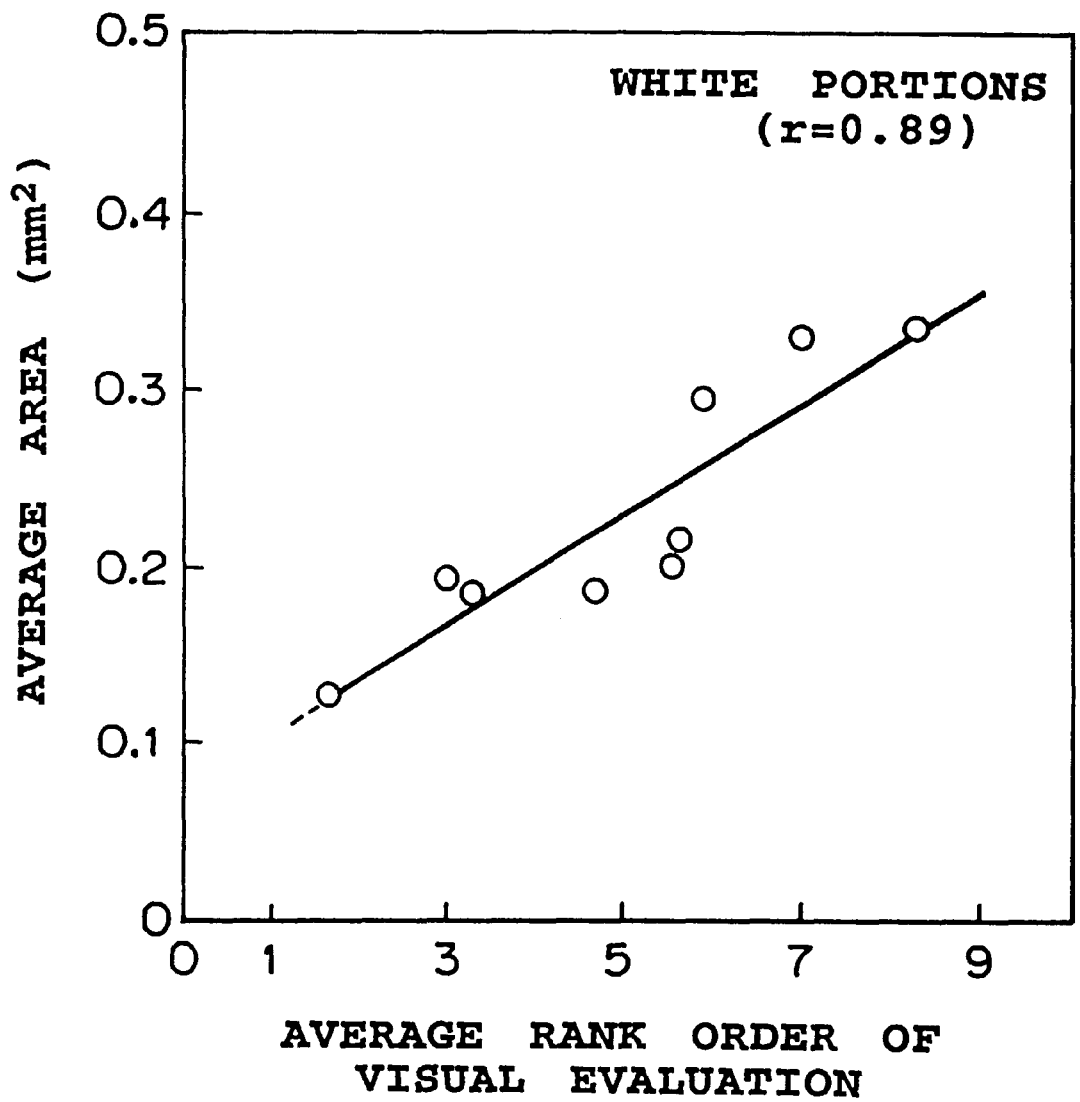
FIG. 19 is a diagram illustrating relations between the visual evaluation and the mean area of white regions of an emphasized image on mat tone coated paper.
Figure 20:
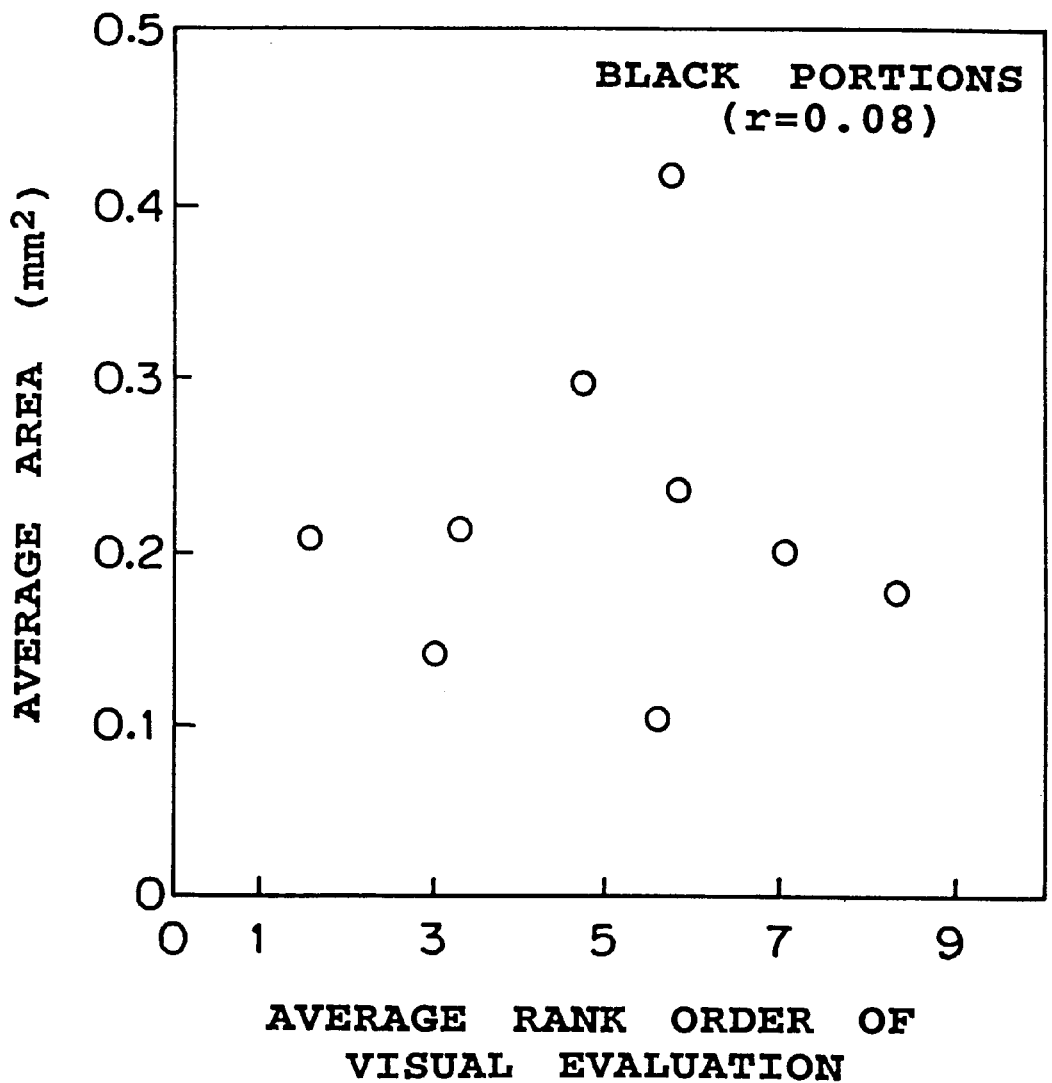
FIG. 20 is a diagram illustrating relations between the visual evaluation and the mean area of black regions of an emphasized image on the mat tone coated paper.
Figure 21:
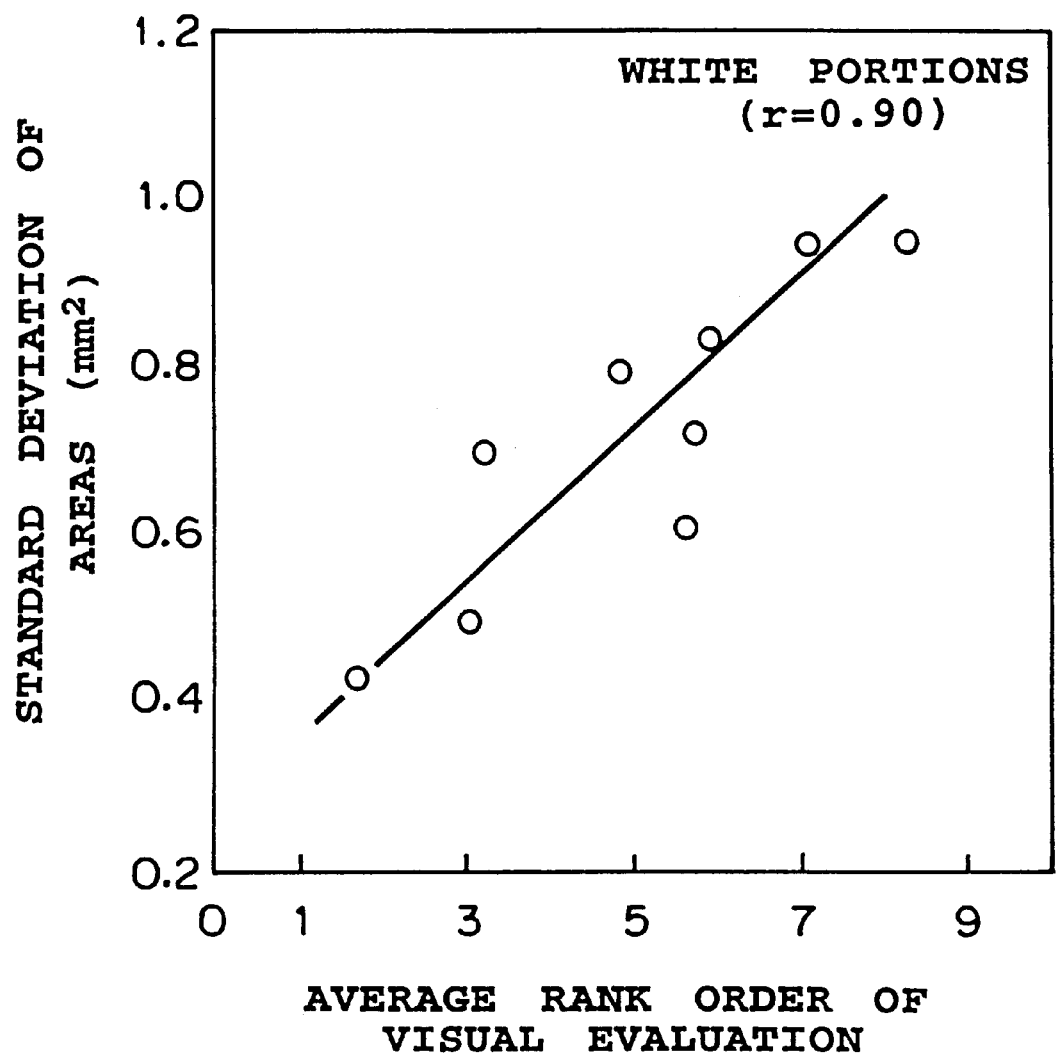
FIG. 21 is a diagram illustrating relations between the visual evaluation and the standard deviation of the areas of white regions of an emphasized image on mat tone coated paper.
Figure 22:
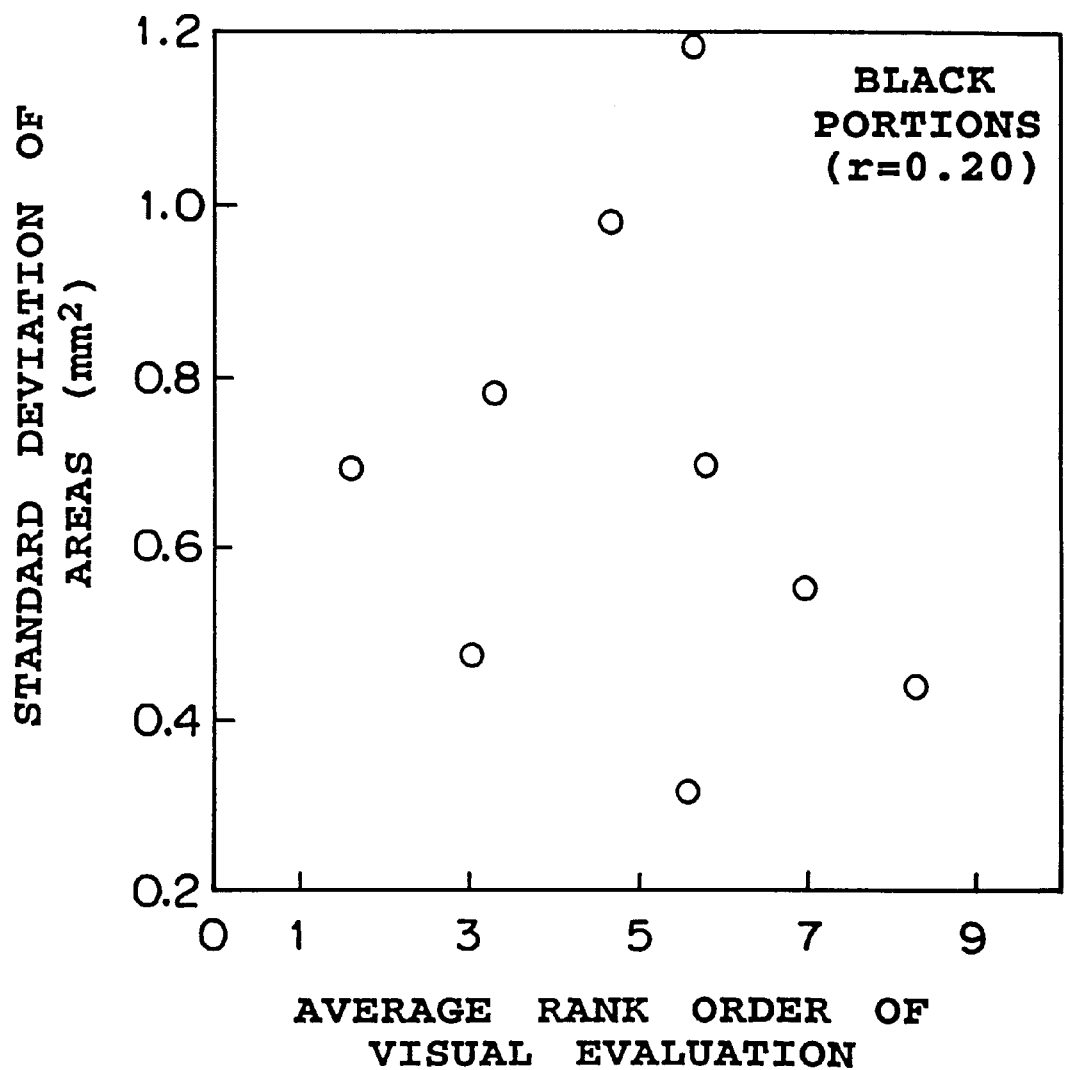
FIG. 22 is a diagram illustrating relations between the visual evaluation and the standard deviation of the areas of black regions of an emphasized image on the mat tone coated paper.

In this connection, it is known that there are two kinds of coated papers: gloss tone coated paper with a high gloss value (about 45%–85%); and mat tone coated paper with a low gloss value (about 0 to 30%). With the gloss irregularity of an image acquired by picking up the gloss tone coated paper, it has already been mentioned referring to FIGS. 5 and 6 that the image data in the dark portions (black portions) have higher correlation with the visual evaluation than the image data in the bright portions (white portions). With this in mind, the mat tone coated paper is examined, and its results are as shown in FIGS. 19 and 20. FIG. 19 shows the relations between the mean area of the closed regions of the white portions and the rank orders of the visual evaluation, whereas FIG. 20 shows the relations between the mean area of the closed regions of the black portions and the rank orders of the visual evaluation. According these results, the correlation coefficient (the values of r) in white portion data is larger than the coefficient in the black portion data. As a result, it is seen that the white portion data is better for the calculation of distribution in case the of mat tone coated paper. Thus, to obtain good measured results according to the kind of coated papers, users are requested to designate any one of gloss tone coated paper, mat tone coated paper and paperboard from the key board of the image analyzer 120. The CPU in the image analyzer 120 calculates the areas and the distribution of areas using the image data of closed black portions or the closed white portions in accordance with the kind of paper designated from keyboard.

In the above examples, the mean area of closed regions and the standard deviation of the areas were used independently as the data showing the distribution of areas. However, it was found that the degree of gloss irregularity and printing unevenness can better be shown by using the product of the mean of the areas of the closed regions and the standard deviation of the areas (the mean area of closed regions x the standard deviation) as the measure expressing the gloss irregularity and printing unevenness.

Tables 6–8 show the correlation coefficients between the mean rank orders of visual evaluation and the following values: that is, the mean areas, the standard deviations, and the products of the mean areas and their standard deviations. Changes of these data are shown when gloss papers with different gloss values were examined. Table 7 shows the changes of the above data when the printing unevenness of monochromatic Chinese black halftone portions were tested. Table 8 shows the changes of the above data when the printing unevenness of monochromatic crimson halftone portions were tested.

TABLE 6

| Gloss values of gloss tone coated paper | | | | | |
|---|---|---|---|---|---|
| Grade | A0 | A1 | A2 | A2 | A3 |
| Basis weight (g/m$^2$) | 128 | 128 | 128 | 79 | 70 |
| Number of samples | 5 | 7 | 5 | 9 | 7 |
| Gloss on white paper (%) | 76–83 | 72–78 | 60–67 | 56–71 | 47–59 |
| Correlation coefficient | | | | | |
| with standard deviation black portion areas | 0.96 | 0.90 | 0.95 | 0.97 | 0.94 |
| with the average of black portion areas | 0.97 | 0.90 | 0.97 | 0.97 | 0.89 |
| with black portions (area x standard deviation) | 0.98 | 0.97 | 0.98 | 0.96 | 0.94 |
| with standard deviation of gradation | 0.03 | 0.63 | 0.42 | 0.35 | 0.64 |

TABLE 6-continued

| Gloss values of gloss tone coated paper | | | | | |
|---|---|---|---|---|---|
| with coefficient of variation of gradation | 0.86 | 0.59 | 0.86 | 0.72 | 0.85 |
| Range | | | | | |
| Standard deviation of black portion areas (mm$^2$) | 0.21–0.57 | 0.24–0.56 | 0.30–0.79 | 0.31–1.10 | 0.46–0.76 |
| Average of black portion areas (mm$^2$) | 0.10–0.20 | 0.12–0.26 | 0.18–0.32 | 0.17–0.46 | 0.23–0.32 |
| Equivalent circle diameter of black portions (mm$^2$) | 0.35–0.50 | 0.39–0.58 | 0.48–0.64 | 0.47–0.77 | 0.54–0.64 |

TABLE 7

| Type | A0 | A1 | A2 | A3 |
|---|---|---|---|---|
| Average of black portion areas | 0.93 | 0.95 | 0.88 | 0.95 |
| Standard deviation of black portion areas | 0.92 | 0.94 | 0.81 | 0.95 |
| Product of average and deviation | 0.93 | 0.93 | 0.93 | 0.95 |
| Average of white portion areas | 0.59 | 0.91 | 0.90 | 0.81 |
| Standard deviation of white portion areas | 0.44 | 0.87 | 0.87 | 0.70 |
| Product of average and deviation | 0.53 | 0.90 | 0.92 | 0.76 |
| Coefficient of variation of gradation | 0.70 | 0.95 | 0.20 | 0.26 |
| Standard deviation of gradation | 0.71 | 0.95 | −0.40 | 0.38 |
| Equivalent circle diameter of black portion (mm) | 0.44–0.54 | 0.43–0.59 | 0.48–0.59 | 0.54–0.62 |

TABLE 8

| Type | A0 | A1 | A2 | A3 |
|---|---|---|---|---|
| Average of black portion areas | 0.89 | 0.97 | 0.91 | 0.86 |
| Standard deviation of black portion areas | 0.80 | 0.94 | 0.80 | 0.94 |
| Product of average and deviation | 0.87 | 0.98 | 0.89 | 0.91 |
| Coefficient of variation of gradation | 0.90 | 0.30 | −0.08 | 0.05 |
| Standard deviation of gradation | 0.77 | 0.06 | 0.10 | 0.10 |
| Equivaient circle diameter of black portions (mm) | 0.41–0.45 | 0.49–0.58 | 0.49–0.54 | 0.42–0.49 |

Therefore, in the image analyzer 120, the products of the mean areas of the closed regions and their standard deviations are calculated by the CPU. The values themselves may be regarded as the measured values, or the values are converted into levels 1–10, and its results are adopted as the measured results.

In addition to this embodiment, the following example can be implemented.

(1) Although the processings in the first and second embodiments have been explained as far as the measurement of the gloss irregularity and printing unevenness, the appearance inspection can also be achieved automatically using these measurement results. In this case, the presence and absence of defects is detected by comparing the measured parameter values with a predetermined threshold. It is recommended to show the emphasized image on a display in addition to the inspected results.

(2) The following methods can be used for visually outputting the measured results of the gloss irregularity and printing unevenness.

(a) The calculated results can be numerically output with a display or a printer.

(b) The calculated results can be graphically output with a display or a printer.

(c) The degree of the gloss irregularity or printing unevenness can be converted into numerical values by numerical processing using a plurality of parameters. In correspondence with these values, messages such as "large", "medium", or "small" expressing the degree of gloss irregularity or printing unevenness may be displayed.

(3) Conventional techniques can be used to detect closed regions. The foregoing embodiments described its example, which counts the number of pixels in the black portions and the white portions in an emphasized image to detect the closed regions in the image, thereby obtaining the areas of these portions. The black portions are defined as regions with gradation levels of 0 and 1, whereas the white portions are defined as regions with gradation levels of 254 and 255. Another method can also be used to detect closed regions and calculate their areas. In this method, contour lines are extracted out of the emphasized image using the well-known counter line extraction processing, and the areas of the closed regions are obtained by counting the number of pixels inside the contour line.

(4) If it is necessary to make clear the boundary of regions of gloss irregularity or printing unevenness, it is recommended to display the closed regions with their contours emphasized.

INDUSTRIAL APPLICABILITY

In the first, second and third aspects of the present invention, the accuracy of measurement is increased by grasping the printing unevenness in the form of the closed regions in the acquired image, and by expressing the degree of distribution of the areas of the closed regions in terms of, for example, the mean area, the standard deviation, the coefficient of variation, the number of white portions or dark portions per unit area, or the product of the mean area and the standard deviation. In particular, the mean area, the standard deviation and the product of the mean area and the standard deviation are preferable as a quantified value of the visual evaluation.

In the fourth aspect of the present invention, the inspection object is paper, and the degree of printing unevenness of printed portions on the paper is determined by the image processing.

In the fifth aspect of the present invention, the measurement of the printing unevenness of the gloss tone coated paper, mat tone coated paper and paperboard becomes possible. A quantified value is preferable to represent the degree of printing unevenness in halftone areas of the inspection object. Above all, it is preferable that the dark regions be detected as regions representing the printing unevenness in the gloss tone coated paper, mat tone coated paper and paperboard.

In the sixth aspect of the present invention, in addition to any one of the first, third, and fourth aspects of the present invention, the accuracy of measurement of printing unevenness is increased by emphasizing the brightness and darkness of the acquired image.

In the seventh aspect of the present invention, the measured result of printing is obtained by calculating the image areas of either the bright or dark portions which form the closed regions.

In the eighth aspect of the present invention, besides the seventh aspect of the present invention, transmitting only the diffused reflected light to the image pickup device can increase the accuracy of measurement of printing unevenness This is because the inspection of the printing unevenness is carried out by observing the ink density, or more precisely, the unevenness of dot density, which depends on the diffused reflected light from the surface of the printed paper. Incidentally, the fine gloss irregularities of the coated paper are due to the regularly reflected light. Thus, this differs from the gloss irregularity due to the diffused reflected light, which causes the printing unevenness.

In the ninth aspect of the present invention, the accuracy of measurement of the gloss irregularity is increased by expressing the degree of the gloss irregularity by the product of the mean area and the standard deviation of the areas of the closed regions derived from the acquired image. It is preferable to adopt the mean area, the standard deviation and the product of the mean area and the standard deviation as a quantified value corresponding to the visually observed result of the gloss irregularity.

In the tenth aspect of the present invention, the inspection object is the mat paper, and the desirable accuracy of the measurement of the gloss irregularity of the mat paper is obtained by calculating the areas of the bright portions forming the closed regions.

In the eleventh aspect of the present invention, the object of inspection is the paperboard, and the desirable accuracy of measurement of the gloss irregularity on the paperboard is obtained by calculating the areas of the dark portions forming the closed regions. It is preferable with the gloss tone coated paper and paperboard to detect the dark portions as regions representing gloss irregularity, whereas with the mat coated paper, the bright portions.

In the twelfth aspect of the present invention, besides the tenth or eleventh aspect of the present invention, the accuracy of measurement of the gloss irregularity is increased by expressing the degree of the gloss irregularity by the mean area, or the standard deviation of the areas.

In the thirteenth aspect of the present invention, the accuracy of measurement of the gloss irregularity is increased by selecting the data of the closed regions of either the bright portions or the dark portions in accordance with the kind of paper.

In the fourteenth aspect of the present invention, besides the thirteenth aspect of the present invention, the measurement of the gloss irregularity is possible with the gloss tone coated paper, mat tone coated paper and paperboard.

In the fifteenth aspect of the present invention, besides the fourteenth aspect of the present invention, the accuracy of measurement of the gloss irregularity is increased by using the image data of the closed regions in the dark portions for the gloss tone coated paper.

In the sixteenth aspect of the present invention, besides the fourteenth aspect of the present invention, the accuracy of measurement of the gloss irregularity is increased by using the image data of the closed regions in the bright portions for the mat tone coated paper.

In the seventeenth aspect of the present invention, besides the fifteenth aspect of the present invention, the accuracy of measurement of the gloss irregularity is increased by using the image data of the closed regions in the dark portions for the paperboard.

In the eighteenth aspect of the present invention, besides any one of the ninth, tenth and eleventh aspect of the present invention, the accuracy of measurement of the gloss irregularity is increased by emphasizing the brightness and darkness of the acquired image.

What is claimed is:

1. A method of measuring print unevenness by acquiring an image of an object with an image pickup device, said measuring method comprising the steps of:

detecting, in the acquired image, bright regions or dark regions forming closed regions, wherein the detecting step is carried out by an image analyzer and further includes a step of emphasizing brightness when detecting the bright regions and darkness when detecting the dark regions;

obtaining areas of said closed regions;

calculating a distribution of said areas; and adopting a result of the step of calculating as a quantified value of measured results of the print unevenness.

2. The method of measuring print unevenness as claimed in claim 1, wherein said distribution of said areas is a mean of said areas or a standard deviation of said areas.

3. A method of measuring print unevenness by acquiring an image of an object with an image pickup device, said measuring method comprising the steps of:

detecting, in the acquired image, bright regions or dark regions forming closed regions, said closed regions being considered to represent print unevenness of said object, wherein the detecting step is carried out by an image analyzer and further includes a step of emphasizing brightness when detecting the bright regions and darkness when detecting the dark regions; and calculating a product of a mean of areas of said closed regions and a standard deviation of areas of said closed regions as a qualified value representative of the printing unevenness.

4. A method of measuring print unevenness by acquiring an image of a surface of paper with an image pickup device, said measuring method comprising the steps of:

detecting, in the acquired image, bright regions or dark regions forming closed regions, wherein the detecting step is carried out by an image analyzer and further including a step of emphasizing brightness when detecting the bright regions and darkness when detecting the dark regions;

obtaining areas of said closed regions;

calculating a distribution of said areas; and adopting a result of the step of calculating as a quantified value representing the print unevenness.

5. The method of measuring print unevenness as claimed in claim 4, wherein a kind of said paper is one of gloss tone coated paper, mat tone coated paper, and paperboard.

6. An apparatus for measuring print unevenness comprising:

image pickup means for acquiring an image of an object;

detecting means for detecting, in an acquired image, bright regions or dark regions forming closed regions, wherein brightness and darkness of the acquired image are emphasized;

area obtaining means for obtaining areas of said closed regions;

calculating means for calculating a distribution of said areas, and for outputting a calculating result as a measured result of the print unevenness.

7. The measuring apparatus as claimed in claim 6, further comprising a polarization filter which transmits diffused reflected light from said object to said acquiring means.

8. A method of measuring gloss irregularity of an object by acquiring an image of the object with an image pickup device, said measuring method comprising the steps of:

detecting, in the acquired image, bright regions or dark regions forming closed regions, wherein the detecting step is carried out by an image analyzer and further includes a step of emphasizing brightness when detecting the bright regions and darkness when detecting the dark regions; and calculating a product of a mean of areas of said closed regions and a standard deviation of areas of said closed regions as a quantified value representative of the gloss irregularity.

9. A method of measuring gloss irregularity by acquiring an image of a surface of mat paper with an image pickup device, said measuring method comprising the steps of:

detecting, in an acquired image, bright regions forming closed regions, wherein the detecting step further includes a step of emphasizing brightness when detecting the bright regions and darkness when detecting the dark regions;

obtaining areas of said closed regions;

calculating a distribution of said areas; and adopting a result of the step of calculating as a quantified value representing said gloss irregularity, wherein said steps are carried out by an image analyzer.

10. A method of measuring gloss irregularity by acquiring an image of a surface of paperboard with an image pickup device, said measuring method comprising the steps of:

detecting, in an acquired image, dark regions forming closed regions, wherein the detecting step is carried out by an image analyzer and further includes the step of emphasizing brightness when detecting the bright regions and darkness when detecting the dark regions;

obtaining areas of said closed regions;

calculating a distribution of said areas; and adopting a result of the step of calculating as a quantified gloss irregularity.

11. The method of measuring gloss irregularity as claimed in claim 9 or 10, wherein said distribution of said areas is a mean of said areas or a standard deviation of said areas.

12. A method of measuring gloss irregularity by acquiring an image of a coated paper surface with an image pickup device, and carrying out information processing on the acquired images with an image analyzer, thereby adopting a result of the information processing as an indication of the gloss irregularity, said measuring method comprising the steps of:

providing said image analyzer with information on a kind of the paper and based on the provided information identifying selected ones of bright regions and dark regions of the acquired image, detecting, in the acquired image, closed regions of said selected bright regions or dark regions in accordance with the kind of said paper, wherein the detecting step is carried out by said analyzer and further includes a step of emphasizing brightness when detecting the bright regions and darkness when detecting the dark regions;

obtaining areas of said closed regions;

calculating a distribution of said areas; and adopting a result of the step of calculating as a quantified gloss irregularity.

13. The method of measuring gloss irregularity as claimed in claim 12, wherein a kind of said paper is one of gloss tone coated paper, mat tone coated paper, and coated paperboard.

14. The method of measuring gloss irregularity as claimed in claim 13, wherein said closed regions are dark regions of said acquired image in said gloss tone coated paper.

15. The method of measuring gloss irregularity as claimed in claim 13, wherein said closed regions are bright regions of said acquired image in said mat tone coated paper.

16. The method of measuring gloss irregularity as claimed in claim 13, wherein said closed regions are dark regions of said acquired image in said paperboard.

\* \* \* \* \*